United States Patent
Daniels et al.

(10) Patent No.: US 10,893,911 B2
(45) Date of Patent: Jan. 19, 2021

(54) AUTOMATED IMAGE CROPPING FOR ENHANCED AUTOMATIC DEVICE-TO-IMAGE REGISTRATION

(71) Applicant: Canon U.S.A., Inc., Melville, NY (US)

(72) Inventors: Barret Daniels, Cambridge, MA (US); Takahisa Kato, Brookline, MA (US)

(73) Assignee: Canon U.S.A., Inc., Melville, NY (US)

( * ) Notice: Subject to any disclaimer, the term of this patent is extended or adjusted under 35 U.S.C. 154(b) by 120 days.

(21) Appl. No.: 16/194,012

(22) Filed: Nov. 16, 2018

(65) Prior Publication Data

US 2019/0159844 A1  May 30, 2019

Related U.S. Application Data

(60) Provisional application No. 62/590,645, filed on Nov. 26, 2017.

(51) Int. Cl.
*A61B 34/20* (2016.01)
*G06T 7/33* (2017.01)
(Continued)

(52) U.S. Cl.
CPC .............. *A61B 34/20* (2016.02); *A61B 5/055* (2013.01); *A61B 6/032* (2013.01);
(Continued)

(58) Field of Classification Search
CPC ......... A61B 34/20; A61B 90/11; A61B 5/055; A61B 6/032; A61B 17/3403;
(Continued)

(56) References Cited

U.S. PATENT DOCUMENTS 5,427,099 A   6/1995  Adams
5,613,013 A   3/1997  Schuette
(Continued)

FOREIGN PATENT DOCUMENTS

JP    2001017422 A    1/2001
JP    2005-136981 A   5/2005
(Continued)

OTHER PUBLICATIONS

Frangi, A., et al., "Multiscale Vessel Enhancement Filtering", in Medical Image Computing and Computer-Assisted Interventation MICCAI98 (W. Wells, A. Colchester, and S. Delp, eds.), vol. 1496 of Lecture Notes in Computer Science, pp. 130-137, Springer Berlin Heidelberg, 1998.
(Continued)

*Primary Examiner* — Leon Viet Q Nguyen
(74) *Attorney, Agent, or Firm* — Canon U.S.A., Inc. IP Division

(57) ABSTRACT

Systems, methods, and computer-readable media are provided. Some embodiments include obtaining image data of a subject and a medical device, the medical device including fiducial markers, wherein the image data includes three-dimensional image data. Information is generated representing a three-dimensional shape based on a planned insertion point for performing a medical procedure. A cropping process is applied to the image data to generate cropped image data based on the three-dimensional shape. In some embodiments, the cropped image data includes image data of at least two of the fiducial markers. Fiducial marker objects are detected within the cropped image data, and the fiducial marker objects are registered by matching a model of the fiducial markers with the fiducial marker objects.

20 Claims, 18 Drawing Sheets

(51) Int. Cl.

| | |
|---|---|
| *G06T 3/40* | (2006.01) |
| *A61B 5/055* | (2006.01) |
| *A61B 6/03* | (2006.01) |
| *A61B 17/34* | (2006.01) |
| *A61B 90/11* | (2016.01) |
| *A61B 90/00* | (2016.01) |
| *A61B 34/10* | (2016.01) |

(52) U.S. Cl.
CPC .......... *A61B 17/3403* (2013.01); *A61B 90/11* (2016.02); *G06T 3/40* (2013.01); *G06T 7/344* (2017.01); *A61B 2034/107* (2016.02); *A61B 2034/2051* (2016.02); *A61B 2034/2065* (2016.02); *A61B 2090/374* (2016.02); *A61B 2090/3762* (2016.02); *A61B 2090/3954* (2016.02); *A61B 2090/3966* (2016.02); *G06T 2207/10028* (2013.01); *G06T 2207/10081* (2013.01); *G06T 2207/10088* (2013.01); *G06T 2207/30204* (2013.01)

(58) Field of Classification Search
CPC ...... A61B 2304/107; A61B 2034/2051; A61B 2034/2065; A61B 2090/374; A61B 2090/3762; A61B 2090/3954; A61B 2090/3966; G06T 7/344; G06T 3/40; G06T 2207/10028; G06T 2207/10081; G06T 2207/10088; G06T 2207/30204
See application file for complete search history.

(56) References Cited

U.S. PATENT DOCUMENTS

| | | | |
|---|---|---|---|
| 6,975,896 B2 | 12/2005 | Ehnholm | |
| 7,720,522 B2 | 5/2010 | Solar | |
| 8,027,712 B2 | 9/2011 | Sioshansi | |
| 9,125,676 B2 | 9/2015 | Sahini | |
| 9,222,996 B2 | 12/2015 | Fujimoto et al. | |
| 9,408,627 B2 | 8/2016 | Sahini | |
| 2005/0107808 A1 | 5/2005 | Evans | |
| 2007/0167801 A1* | 7/2007 | Webler .................. | A61B 8/445 600/459 |
| 2009/0112082 A1 | 4/2009 | Piferi | |
| 2010/0040263 A1* | 2/2010 | Li ........................... | G06T 5/009 382/128 |
| 2010/0069746 A1 | 3/2010 | St. John | |
| 2010/0082040 A1 | 4/2010 | Sahni | |
| 2010/0266175 A1 | 10/2010 | Seung et al. | |
| 2014/0049629 A1 | 2/2014 | Siewerdsen | |
| 2014/0289605 A1 | 9/2014 | Buelow et al. | |
| 2014/0343416 A1 | 11/2014 | Panescu et al. | |
| 2015/0087965 A1 | 3/2015 | Tokuda | |
| 2015/0098636 A1 | 4/2015 | Bergman | |
| 2015/0125033 A1* | 5/2015 | Murphy .................. | G06T 7/251 382/103 |
| 2015/0125890 A1 | 5/2015 | Wong | |
| 2015/0178917 A1* | 6/2015 | Yang ...................... | A61B 6/032 382/131 |
| 2015/0320513 A1 | 11/2015 | Yoon | |
| 2016/0074063 A1 | 3/2016 | Arimitsu et al. | |
| 2017/0000581 A1* | 1/2017 | Tokuda ................. | G06K 9/6201 |
| 2017/0079720 A1 | 3/2017 | Velusamy et al. | |
| 2017/0100195 A1 | 4/2017 | Velusamy | |
| 2019/0180416 A1* | 6/2019 | Maack ................. | A61B 6/5235 |

FOREIGN PATENT DOCUMENTS

| | | |
|---|---|---|
| JP | 2017023516 A | 2/2017 |
| JP | 2017530758 A | 10/2017 |
| JP | 2018529399 A | 10/2018 |
| WO | 2007100293 A1 | 9/2007 |
| WO | 2017003453 A1 | 1/2017 |

OTHER PUBLICATIONS

Fedorov, A., et al., "3D Slicer as an Image Computing Platform for the Quantitative Imaging Network." Magn Reson Imaging, Nov. 2012, pp. 1323-1341, vol. 30, No. 9.

Antiga, L., "Generalizing vesselness with respect to dimensionality and shape", Insight J., Aug. 3, 2007.

Brown, R.A., "A computerized tomography-computer graphics approach to stereotaxic localization", J Neurosurg., Jun. 1979, pp. 715-720, vol. 50, No. 6.

Busse, H., et al., "Method for Automatic Localization of MR-Visible Markers using Morphological Image Processing and Conventional Pulse Sequences: Feasibility for Image-Guided Procedures", J Magn Reson Imaging. Oct. 2007, pp. 1087-1096, vol. 26, No. 4.

De Oliveira, A., et al., "Automatic Passive Tracking of an Endorectal Prostate Biopsy Device Using Phase-Only Cross-Correlation", Magn Reson Med, 2008, pp. 1043-1050, vol. 59.

Dimaio S.P., et al., "Dynamic MRI Scan Plane Control for Passive Tracking of Instruments and Devices", Med Image Comput Comput Assist Interv. 2007, pp. 50-58, vol. 10 (Pt 2).

Fledilius, W., et al., "Robust automatic segmentation of multiple implanted cylindrical gold fiducial markers in cone-beam CT projections", Med Phys., Dec. 2011, pp. 1323-1341, vol. 38, No. 12.

George, A.K., et al., "Robust automatic rigid registration of MRI and X-ray using external fiducial markers for XFM-guided interventional procedures", Med Phys., Jan. 2011, pp. 125-141, vol. 38, No. 1.

Heilbrun, M.P., et al., "Preliminary experience with Brown-Roberts-Wells (BRW) computerized tomography stereotaxic guidance system", J Neurosurg., Aug. 1983, pp. 217-222, vol. 59, No. 2.

Krieger, A., et al., "An MRI-Compatible Robotic System With Hybrid Tracking for MRI-Guided Prostate Intervention", IEEE Trans Biomed Eng., Nov. 2011, pp. 3049-3060, vol. 58, No. 11.

Krishnan, R., et al., "Automated fiducial marker detection for patient registration in image-guided neurosurgery", Comput Aided Surg., 2003, pp. 17-23, vol. 8, No. 1.

Labadie, R.F., et al., "Submillimetric target-registration error using a novel, non-invasive fiducial system for image-guided otologic surgery", Comput Aided Surg., 2004, pp. 145-153, vol. 9, No. 4.

Lorenz, C., et al. "Multi-scale Line Segmentation with Automatic Estimation of Width, Contrast and Tangential Direction in 2D and 3D Medical Images", 1997. pp. 233-242.

Nederveen, A., et al. "Detection of fiducial gold markers for automatic on-line megavoltage position verification using a marker extraction kernel (MEK)", Int J Radiat Oncol Biol Phys., Jul. 2000, pp. 1435-1442, vol. 47, No. 5.

Smith, L., et al., "Automatic detection of fiducial markers in fluoroscopy images for on-line calibration", Medical Physics, Jun. 2005, pp. 1521-1523, vol. 32, No. 6.

Tokuda, J., et al., "Configurable Automatic Detection and Registration of Fiducial Frames for Device-to-Image Registration in MRI-guided Prostate Interventions", Med Image Comput Comput Assist Interv., 2013, pp. 355-362, vol. 16, No. (0 3).

Tokuda, J., et al., "Integrated navigation and control software system for MRI-guided robotic prostate interventions", Comput Med Imaging Graph., Jan. 2010, pp. 3-8, vol. 34, No. 1.

Tokuda, J., et al., In-bore setup and Software for 3T MRI-guided Transperineal Prostate Biopsy:, Phys Med Biol., Sep. 21, 2012, pp. 5823-5840, vol. 57, No. 18.

Wang, M.Y., et al.,"An Automatic Technique for Finding and Localizing Externally Attached Markers in CT and MR Volume Images of the Head", IEEE Trans Biomed Eng., Jun. 1996, pp. 627-637, vol. 43, No. 6.

Sato, Y., et al., "Three-dimensional multi-scale line filler for segmentation and visualization of curvilinear structures in medical images", Medical Image Analysis, 1998, pp. 143-168, vol. 2, No. 2.

Zheng, G., et al., "Robust automatic detection and removal of fiducial projections in fluoroscopy images: An integrated solution", Med Eng Phys., Jun. 2009, pp. 571-580, vol. 31, No. 5.

Liu, S. et al., "Automatic Multiple-Needle Surgical Planning of Robotic-Assisted Microwave Coagulation in Large Liver Tumor Therapy", PLOS ONE, Mar. 16, 2016, vol. 11, No. 3.

(56) References Cited

OTHER PUBLICATIONS

Morrison, P. R., et al., "MRI-Guided Cryotherapy", Journal of Magnetic Resonance Imaging, 2008, pp. 410-420, vol. 27.

Tokuda, J., et al, "Motion compensation for MRI-compatible patient-mounted needle guide device: estimation of targeting accuracy in MRI-guide kidney cryoablations", Physics in Medicine and Biology, Apr. 13, 2018, vol. 63.

Ben-David, E., et al, "Evaluation of a CT-Guided Robotic System of Precise Percutaneous Needle Insertion", J Vasc Interv Radiol, 2018, pp. 1-7.

Tokuda, J., et al, "OpenIGTLink: an open network protocol for image-guided therapy envimoment", Int J Med Robot, Dec. 2009, pp. 423-434, vol. 5, No. 4.

* cited by examiner

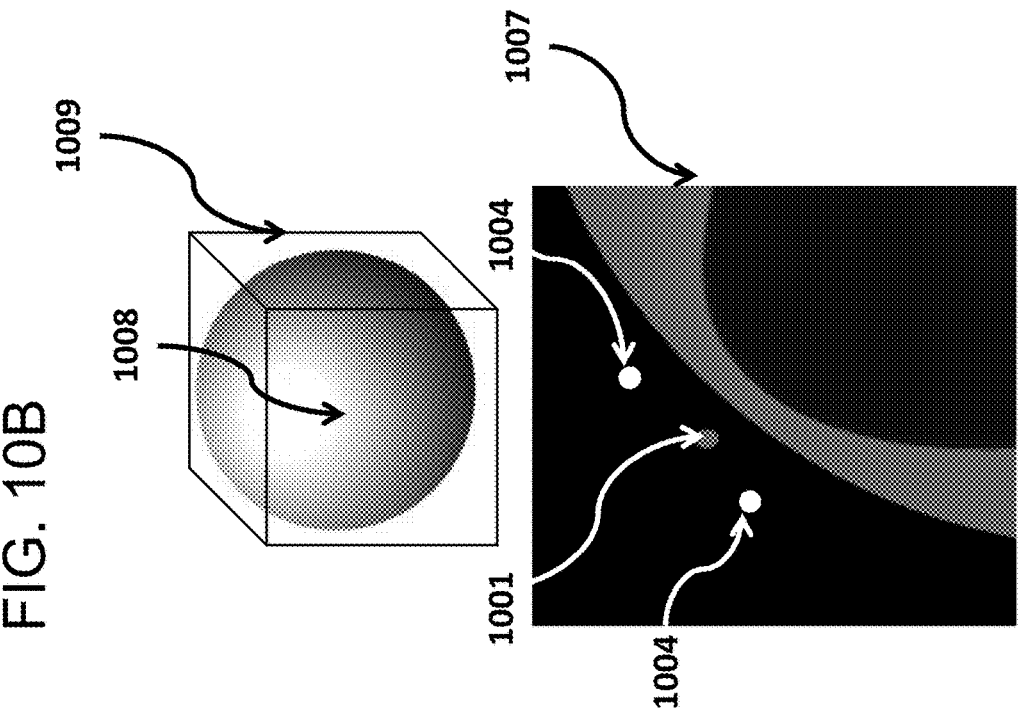
FIG. 10B
FIG. 10C
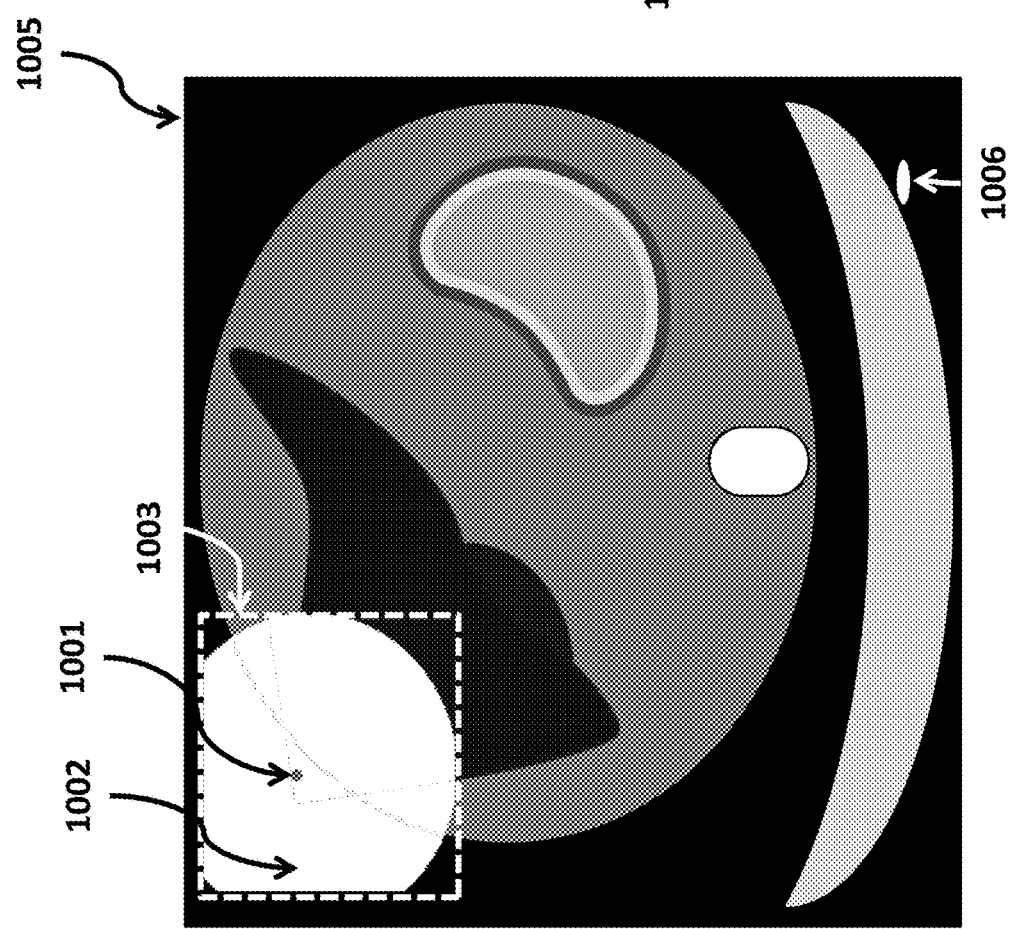
FIG. 10A

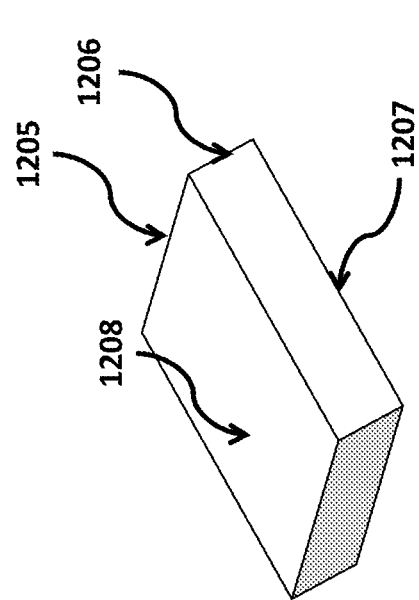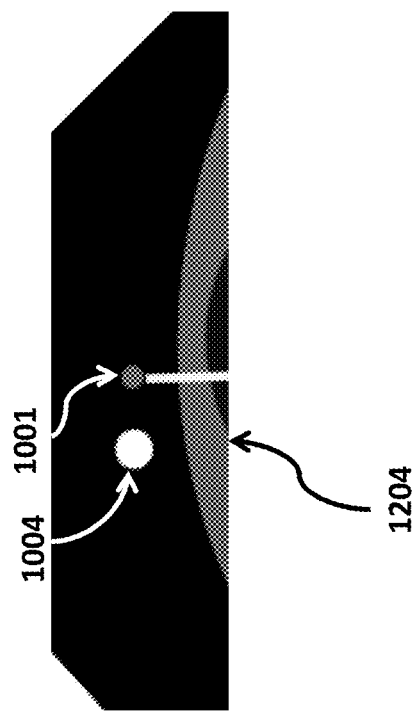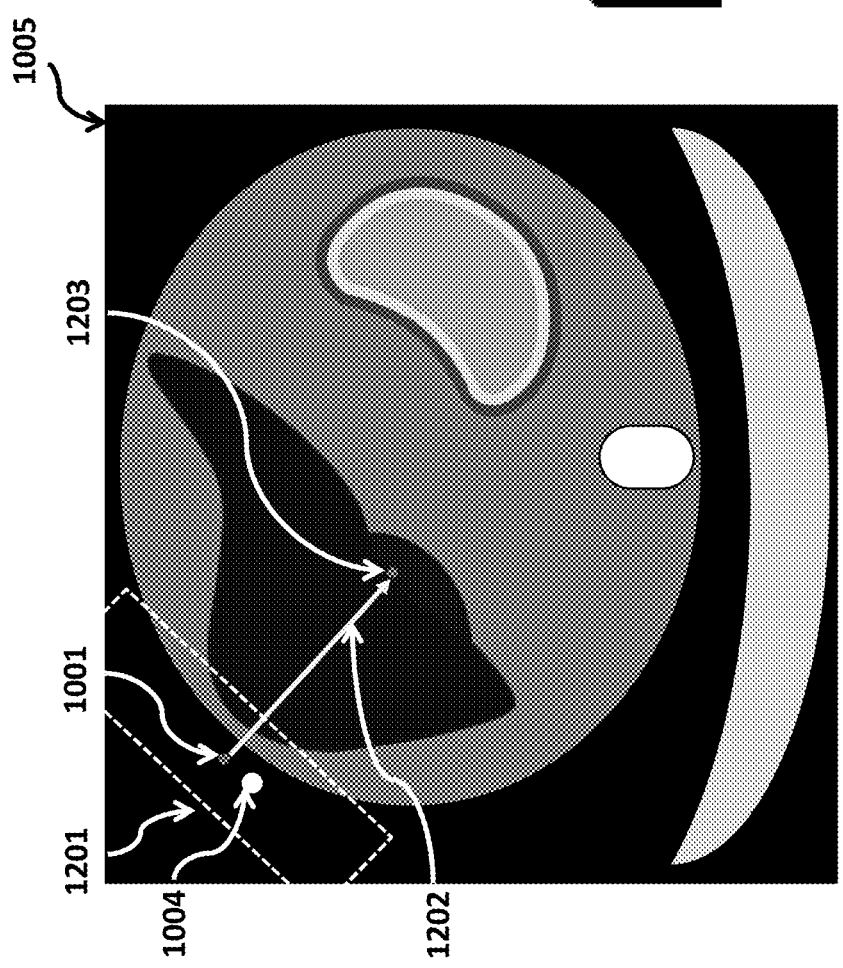
FIG. 12B
FIG. 12C
FIG. 12A

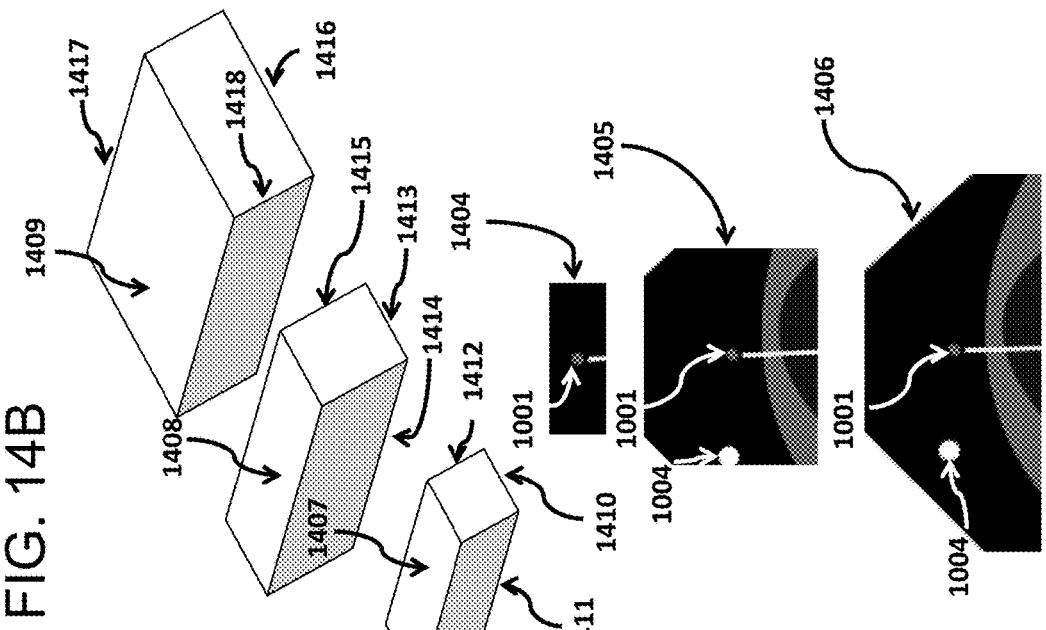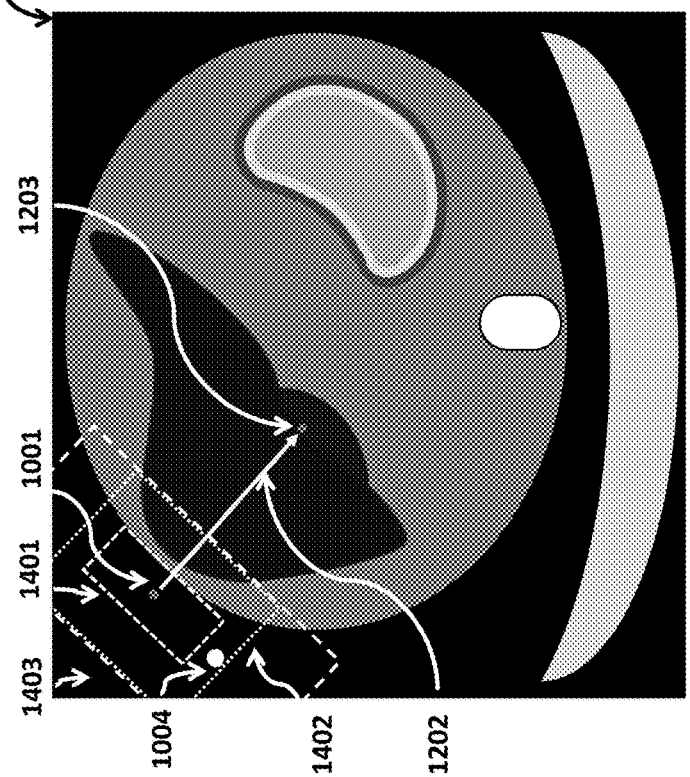
FIG. 14B  FIG. 14C  FIG. 14A

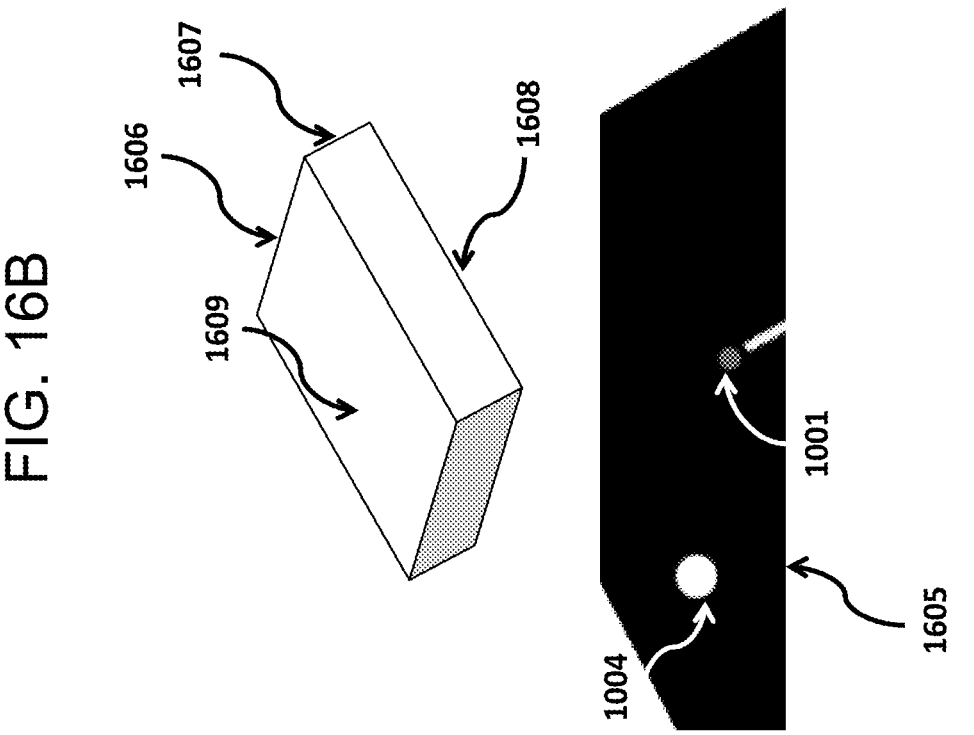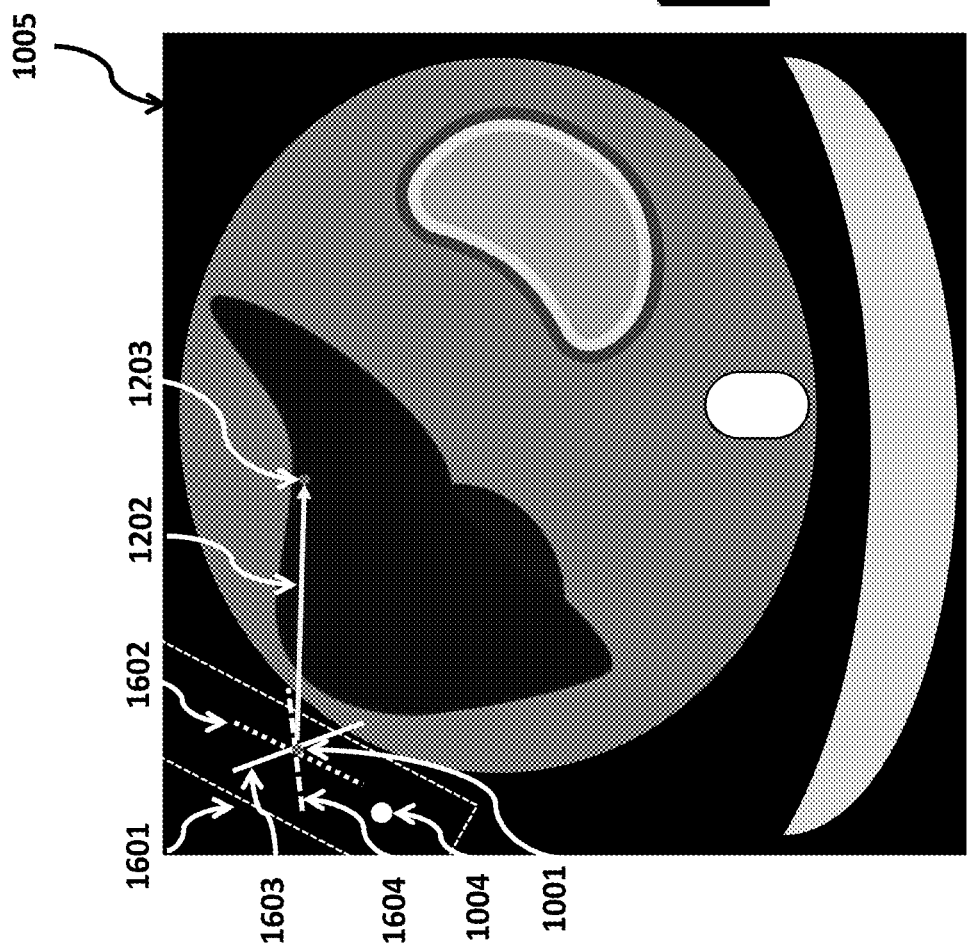

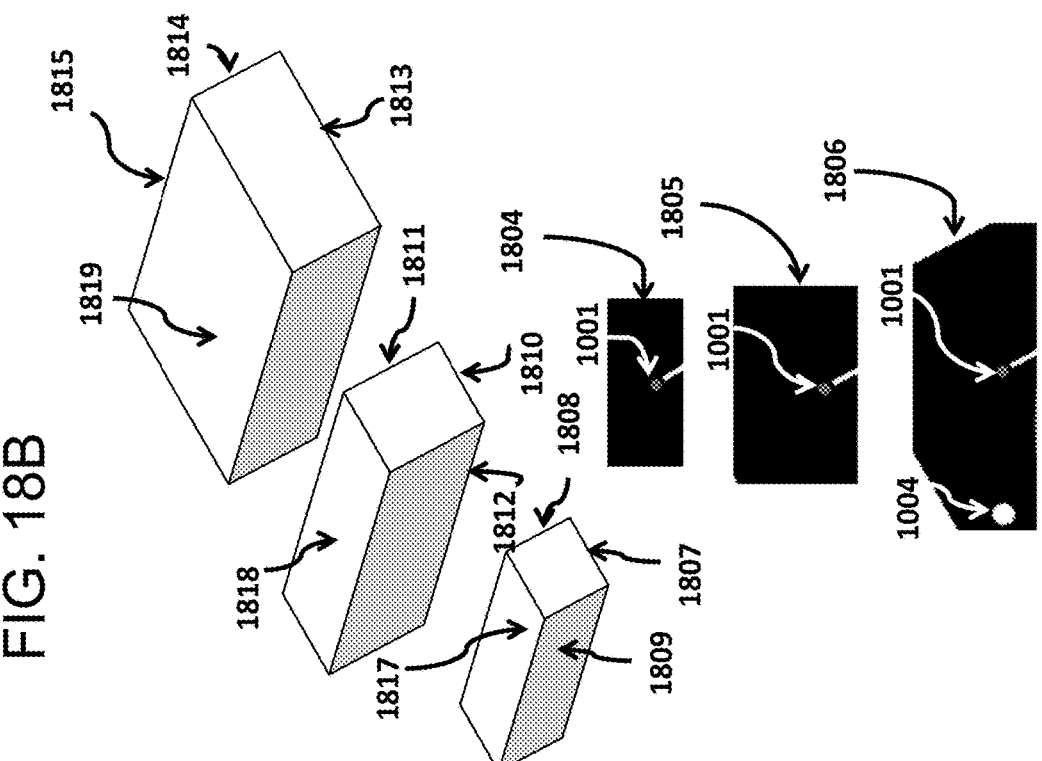
FIG. 18B
FIG. 18C
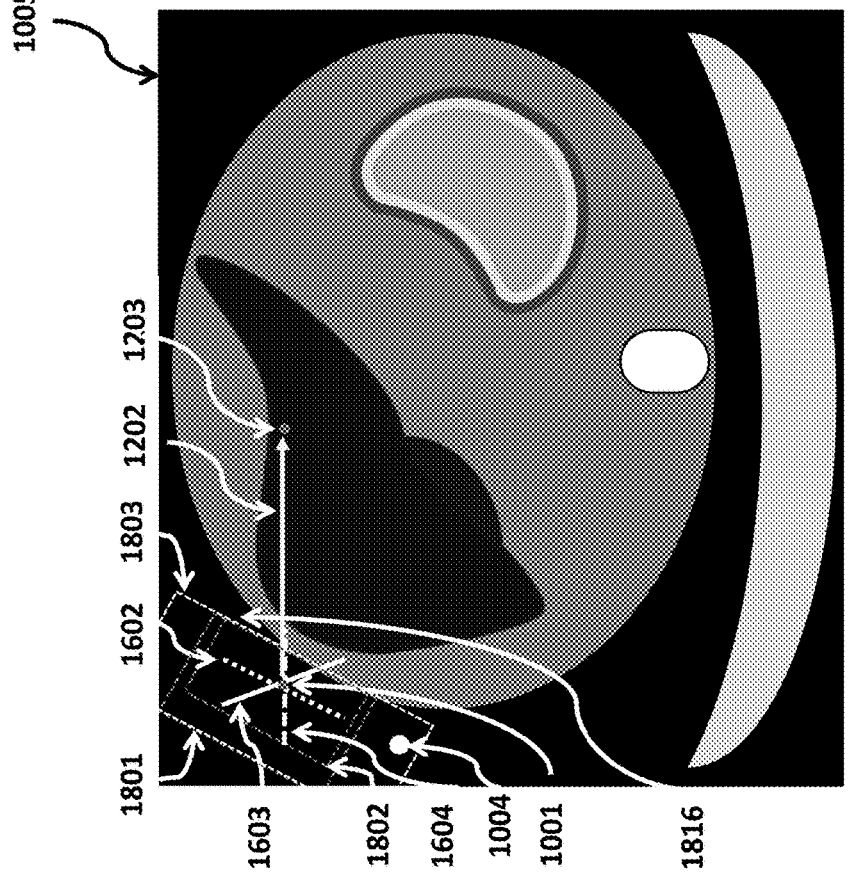
FIG. 18A

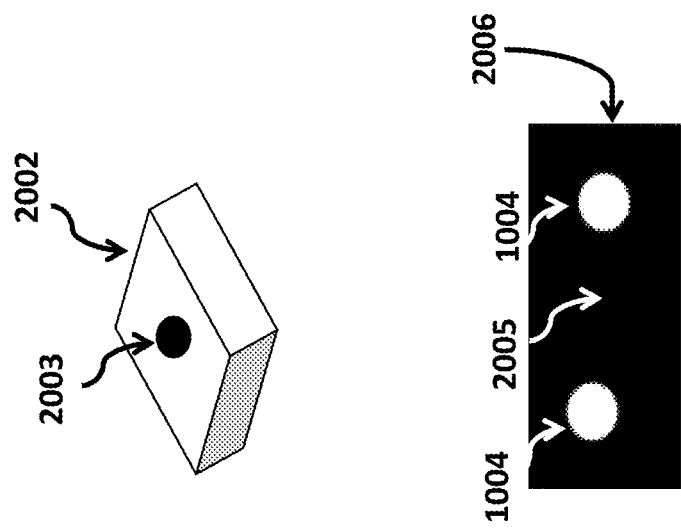
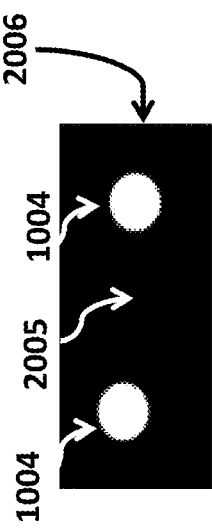
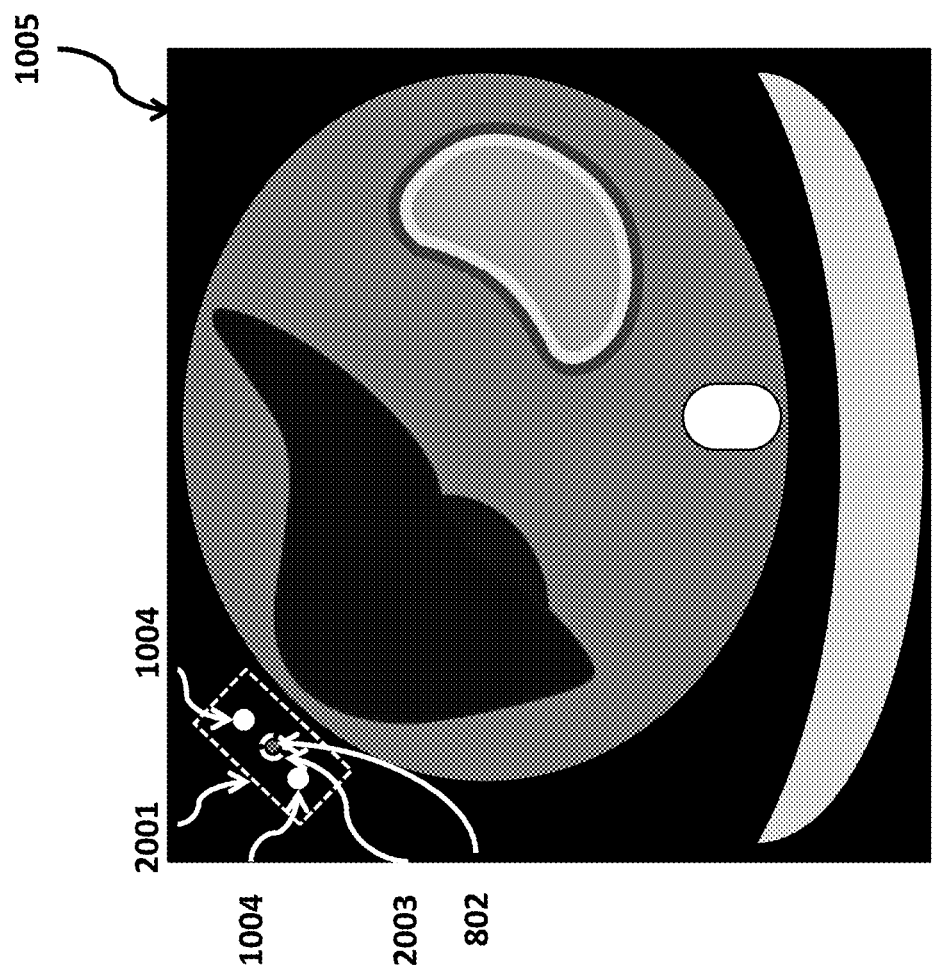
FIG. 20B
FIG. 20C
FIG. 20A

US 10,893,911 B2

AUTOMATED IMAGE CROPPING FOR ENHANCED AUTOMATIC DEVICE-TO-IMAGE REGISTRATION

CROSS-REFERENCE TO RELATED APPLICATIONS

This application claims the benefit of U.S. Provisional Application No. 62/590,645, filed Nov. 26, 2017, which is hereby incorporated by reference herein in its entirety.

FIELD OF THE DISCLOSURE

The present disclosure relates generally to systems, methods, and devices for medical imaging and, more particularly to automated processes for device-to-image registration using fiducial markers.

BACKGROUND INFORMATION

Medical images assist physicians in planning, performing, and post-operative analysis of a procedure. Some imaging modalities that are useful include ultrasound imaging, computed tomography (CT), and magnetic resonance imaging (MRI). Medical images can also be used to assist in navigating various instruments relative to the patient while performing a procedure. It is important to accurately place a device on the patient relative to the treatment area. Fiducial markers may be used to correlate and register determined fiducial points with the fiducial markers in physical space. Registering devices is essential for accurate device placement. However, the detection and registration of fiducial markers are not always simple to achieve due to noise from other sources such as the patient's anatomy. Moreover, automated methods for registering images are still limited and error prone.

Detecting high intensity fiducials in medical images (CT, MRI) for automatic device-to-image registration is essential for interventional instrument guidance devices. With MRI, a user can select a limited rectangular field-of-view; however, CT does not have as much flexibility in setting the imaging field-of-view (generally 50 cm.). Thus, one cannot restrict imaging to the location of the interventional instrument guidance device in CT which complicates accurate and robust automatic fiducial detection and device registration due to other high intensity image features which can be detected mistakenly as fiducials (for example, metal in a patient's bed, metal in padding underneath the patient, and dense anatomical structures such as bone). In conventional systems, fiducial localization typically involves searching the entire image volume for candidate fiducial marker voxels. This can be time consuming and lead to erroneous fiducial detection, thus causing automatic registration to fail in some cases.

It would therefore be desirable to provide a system and method for automating image analysis and image registration that does not suffer from the drawbacks described above.

SUMMARY OF EXEMPLARY EMBODIMENTS

Systems, methods, and computer-readable media for detection and registration of medical images are disclosed. For example, embodiments of this disclosure provide automated image cropping for enhanced automatic device-to-image registration.

Some embodiments include obtaining image data of a subject and a medical device, the medical device including fiducial markers, wherein the image data includes three-dimensional image data. Information is generated representing a three-dimensional shape based on a planned insertion point for performing a medical procedure. A cropping process is applied to the image data to generate cropped image data based on the three-dimensional shape. In some embodiments, the cropped image data includes image data of at least two of the fiducial markers. Fiducial marker objects are detected within the cropped image data, and the fiducial marker objects are registered by matching a model of the fiducial markers with the fiducial marker objects.

Further features of the present disclosure will become apparent from the following description of exemplary embodiments with reference to the attached drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the present disclosure and, together with the description, serve to explain the principles of the present disclosure.

FIGS. 10(A)-10(C) illustrate an example medical image data and cropped image data in accordance with some embodiments.

FIGS. 12(A)-12(C) illustrate an example medical image data and cropped image data in accordance with some embodiments.

FIGS. 14(A)-14(C) illustrate an example medical image data and cropped image data in accordance with some embodiments.

FIGS. 16(A)-16(C) illustrate an example medical image data and cropped image data in accordance with some embodiments.

FIGS. 18(A)-18(C) illustrate an example medical image data and cropped image data in accordance with some embodiments.

FIGS. 20(A)-20(C) illustrate an example medical image data and cropped image data in accordance with some embodiments.

DETAILED DESCRIPTION OF EXEMPLARY EMBODIMENTS

Figure 1:
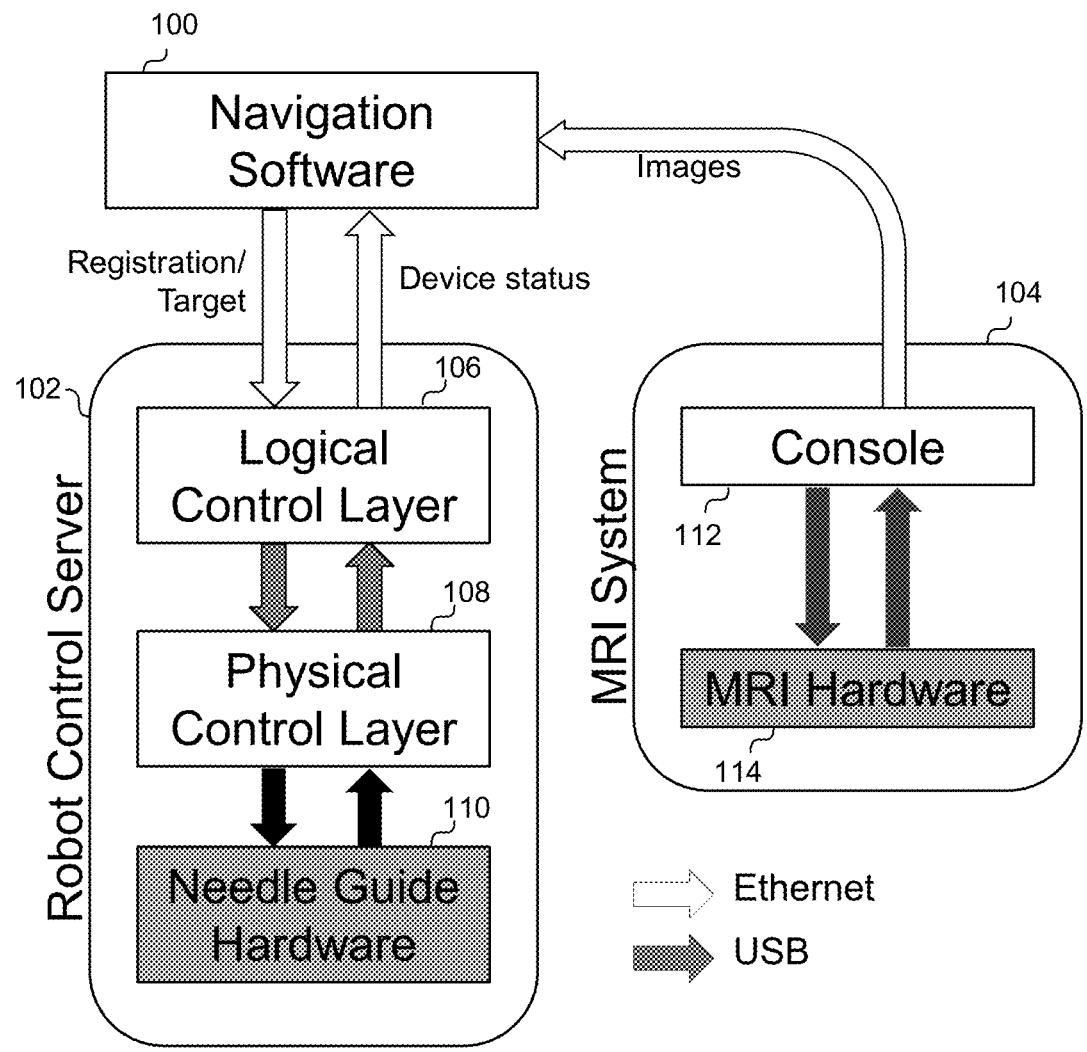
FIG. 1 illustrates an example system diagram of a needle guide robot system including navigation software, robot control server of a needle guide robot, and MRI system including an MRI scanner in accordance with some embodiments.

Exemplary embodiments are described below with reference to the drawings. Systems, methods, and devices for automated medical image cropping for enhanced automatic device-to-image registration are described. Some embodiments include obtaining medical image data of a patient and a medical device including fiducial markers, applying a cropping process to the medical image data to generate cropped image data, detecting fiducial marker objects within the cropped image data, and registering the fiducial marker objects using a model of the fiducial markers. The image data of the patient and the medical device is image data from a tomographic imaging device. In some embodiments, the medical device is a device that is patient-mounted and can, for example, direct or position a needle for entry into the patient.

According to embodiments, the automated medical image cropping process limits a region in which to search for fiducial markers. In some embodiments, the medical image data is cropped and a process is performed for detecting fiducial markers within the cropped image data; and the fiducial marker detection process performed on the cropped region of the image data is not applied to image data outside of the cropped region. Accordingly, in a case where a high intensity image feature is outside of the cropped region, it is possible to avoid identifying the image feature mistakenly as a fiducial marker. Thus, misdetection of fiducial markers can be reduced by automatically limiting a fiducial marker search area before automatic detection and registration is performed on medical image data. In some embodiments, pre-cropping a medical image will speed up automatic registration since image processing algorithms are only run on a portion of the original image rather than on the entire original image.

Some embodiments include performing automated medical image cropping using information associated with pre-procedure planning for a medical procedure. Moreover, some embodiments include performing automatic cropping without user interaction. For example, by using the information associated with pre-procedure planning as an input for medical image cropping, automatic registration is applied to a portion of an image without requiring a user, such as a technologist or doctor, to select a specific portion of the image to which to apply automatic registration. The technologist or doctor may perform their regular planning, and this planning will drive the automatic cropping of a medical image for automatic registration. For example, using the navigation software described herein, a user may specify a target and a planned insertion point at which a needle or other medical tool is to be inserted. By way of example, a physician can define a trajectory of needle placement by specifying the target and skin entry point on a planning image. In some embodiments, the insertion point gives the desired center of the medical device including fiducial markers, and the target gives trajectory to search for a skin plane to construct a cropping shape, such as a sphere or box. Then the cropping shape based on the pre-procedure planning—which is already part of the pre-procedure workflow—can be utilized to automatically crop an acquired medical image.

According to some embodiments, re-registration of a medical device is performed. For example, one or more previous registrations of a medical device is/are used as input(s) to perform registration in the same procedure in order to further limit the cropped area and/or remove metallic needle artifacts which can be detected mistakenly as fiducials. Further refinement of the cropped area helps reduce the chance for fiducial misdetection. Moreover, according to some embodiments, the cropping process is used to eliminate metal artifacts such as the needle from the cropped medical image to prevent the metal artifacts from being accidentally detected as fiducials. In some embodiments, iterative cropping is performed. For example, an initial cropping process may be applied to generate a small cropped area in which to search for fiducial markers. Then, based on a result of the search, the cropped area may be expanded and another search performed. Incremental expansion of the cropped area may continue until optimum results are found.

I. Imaging and Medical Devices

The medical device may be any medical device used in conjunction with tomographic imaging. The tomographic imaging can be, for example, MRI, CT, ultrasound, or other imaging technique. The medical device may be a patient mount device such as, for example, a needle placement device.

One example of a medical device that may be used in combination with systems described herein is described in U.S. Pat. Pub. 2014/0275979, herein incorporated by reference in its entirety. This reference provides an MRI-compatible body-mount needle guide device with double-ring mechanism.

Other medical devices that may use the fiducial markers, systems, and methods as described herein include other free standing or patient-mounted medical devices for needle placement or for tool placement in assisting diagnosis or surgery. For example, a needle guide template, which consists of a grid of holes, is often used to direct a needle into a foci in image-guided prostate biopsy and brachytherapy.

Yet other medical devices that may use the fiducial markers, systems, and methods as described herein include the needle placement device described in U.S. Pat. Pub. 2018/00228568, herein incorporated by reference in its entirety. Additionally, the medical devices described in U.S. Application Ser. Nos. 62/714,566; 62/764,849, 62/746,820 and U.S. Application Ser. No. 62/747,913 may be used in combination with the systems described herein.

II. Robot Control Software

In some embodiments, a software system is provided that has three layers of components including, navigation software 100, logical control layer 106, and physical control interface 108 (FIG. 1). Those components are implemented as independent software processes, and communicate with each other via, for example, Ethernet and Universal Serial Bus (USB). However, in other embodiments, two more of these components are integrated into a single software process.

The details of those three components are as follows:

Navigation Software

The navigation software 100 is the top layer component in the system and is exemplified in FIG. 1. The navigation software 100 works, for example, as a primary user interface for the physician and/or operator. It is implemented as described herein as a plug-in module for 3D Slicer, open-source medical image computing software and, through this or other software, receives images from the MRI system 104 which includes the console 112 and MRI hardware 114, which includes an MRI scanner. The navigation software 100 assists the physician in performing the following tasks.

Needle Placement Planning.

Figure 3:
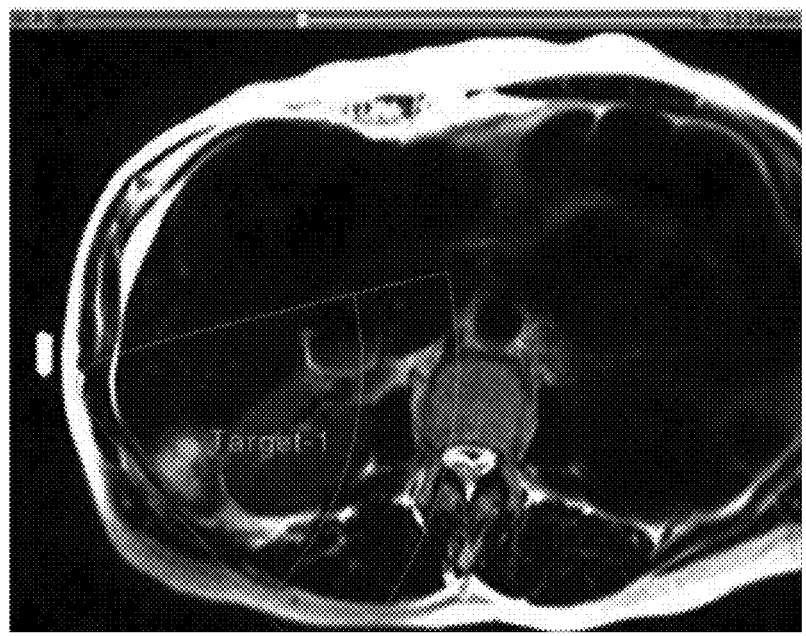
FIG. 3 shows a medical image presented on an example graphical user interface in accordance with some embodiments. The image includes a 3D representation of patient anatomy and information identifying a planned trajectory and target.

The physician can define a trajectory of needle placement by specifying the targets and skin entry point on the planning image. The software displays a section of the planning image along any plane and allows the physician to specify the points by clicking on it with a mouse. Once the trajectory has been defined, it can re-slice the 3D image with a plane along the trajectory so that the physician can find any critical structures and obstacles around the path (FIG. 3). The defined trajectory is transferred to the robot control server 102. The final decision to move the actuator, however, is preferably made by the physician standing by the gantry; the actuators can be powered on only when the physician presses down a footswitch.

Device-to-Image Registration.

The software can automatically detect the markers embedded in the device in the calibration image for the registration of the device to the image coordinate system. Detail of an algorithm that detects and registers the fiducial markers in some embodiments is described below. Once the device is registered, the software overlays the model of the device and its accessible range on the image, so that the operator can confirm that the all targets are in the range (FIG. 3). The linear transformation matrix is transferred to the robot control server 102 over the network using, for example, the OpenIGTLink protocol.

Monitoring and Confirmation of Probe Placement.

Figure 4:
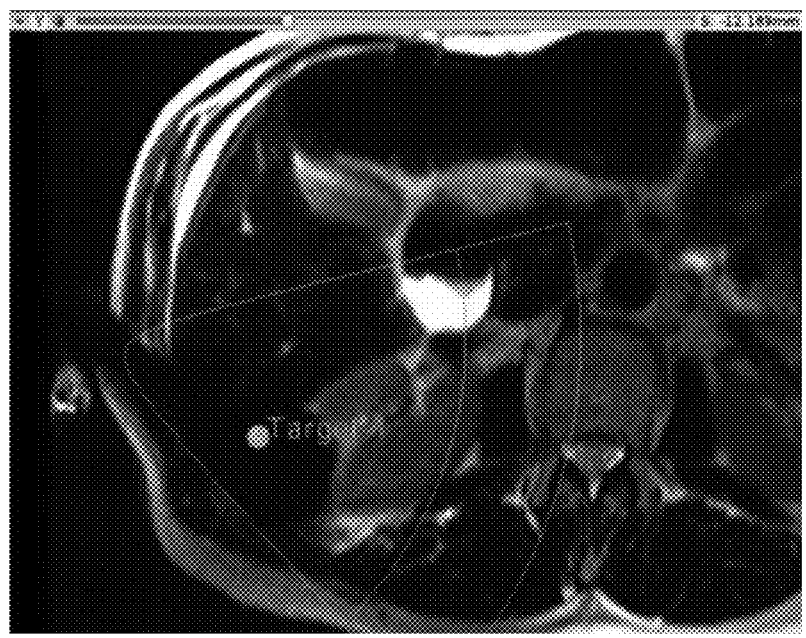
FIG. 4 shows a medical image presented on an example graphical user interface in accordance with some embodiments. The image includes a 3D representation of patient anatomy and an image of a probe inserted into the patient.

The software can be used to visualize the current position and orientation of the device with a 3D model overlaid on the images anytime during the procedure. In addition, it also can display confirmation images that show the probe inserted into the patient with the planned trajectory and target (FIG. 4). Those features allow the physicians to monitor the device and confirm the probe placement.

Logical Control Layer

The Logical Control Layer (LCL) 106 sits in the middle layer of the system and interfaces the navigation software 100 and low-level physical control layer (PCL) 108. This layer of the robot control server 102 can encapsulate the hardware and the kinematic structure of the device, and provide a device-independent application program interface (API) to the upper layer. Therefore, the LCL 106 consists of the following subcomponents:

TCP/IP Network Interface to the Upper Layer.

Through this interface, the LCL 106 receives commands to the hardware from the upper layer including the target position, and provides the current status of the hardware (110) to the upper layer including the current position of the needle guide, and the status of the device. It also provides the required needle insertion depth as a result of kinematics computation (see Kinematics engine below) to the upper layer. In some embodiments, the LCL 106 provides a configuration of the fiducial frame to the upper layer, where fiducial-based device-to-image registration is performed, keeping the upper layer independent from the hardware. In some embodiments, the network interface is compliant with the OpenIGTLink protocol, and thus it can communicate with software compatible with OpenIGTLink.

Kinematics Engine.

In some embodiments, the hardware-independent commands received from the upper layer are translated into the target positions of individual actuators based on the kinematics of the needle guide device, and sent to the PCL 108. Moreover, in some embodiments, current positions of individual actuators received from the PCL 108 are translated to the position and orientation of the needle guide and sent to the upper layer. According to some embodiments, the needle guide device is a manually operated device. For example, needle guide devices that may be used in combination with systems described herein are described in U.S. Pat. No. 9,222,996 and in U.S. Patent Pub. 2018/0228,568, both of which are herein incorporated by reference in their entirety.

Serial Interface to the Lower Layer.

The LCL 106 communicates with the lower layer subcomponent through a universal serial bus (USB). Through this exemplary interface, target positions of individual actuators and other device-specific commands are sent to the PCL 108, while the current status of the device and the encoder readings of individual actuators are sent to the navigation software 100. The information exchanged through this interface is dependent on the kinematic structure, but independent from the physical hardware (e.g. motor drivers and encoders).

Physical Control Layer

The role of the Physical Control Layer (PCL) 108 is to provide an interface that is independent from the physical input/output (I/O), but dependent on the kinematic structure. In some embodiments, the PCL 108 runs on a Linux-based embedded computer equipped with a USB interface for the communication with the LCL 106, and a digital input/output interface for reading inputs from encoders and footswitch and giving the target speeds of individual motors to the motor drivers. Once the controller receives target positions for individual actuators, it performs closed-loop PID control of individual motors to position the two rings at the designated positions. Throughout this process, the PCL 108 can optionally keep sending the current positions of the rings and other device status.

Computing System

Figure 2:
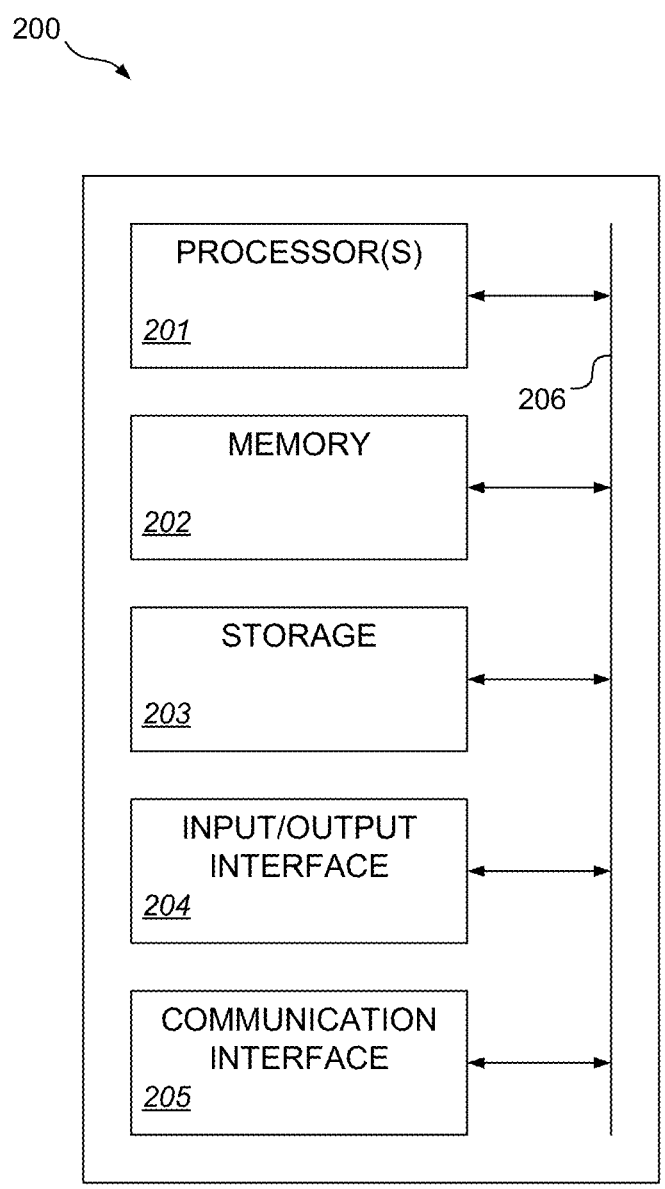
FIG. 2 illustrates an example computing system in accordance with some embodiments.

FIG. 2 illustrates an example computing system 200. The computing system 200 includes the navigation software 100. The various programs and data—for example, software modules, libraries, tools, user interface elements, or other components—of the navigation software 100 reside in the computing system 200 in any suitable manner, in accordance with various embodiments. For example, these components may reside in one or multiple storage locations. The components of the navigation software 100 may be provided as part(s) of a single software application or as a plurality of stand-alone software applications. The computing system 200 provides access to the navigation software 100. In some embodiments, the navigation software 100 executing on the computing system 200 performs one or more steps of one or more methods described or illustrated herein, or provides functionality described or illustrated herein. For example, programs of the navigation software 100 may include instructions that, when executed by one or more processors, cause the computing system 200 to perform an automatic cropping process to medical image data to generate cropped image data, and then detect fiducial marker objects within the cropped image data, and register the fiducial marker objects using a model of the fiducial markers.

The term computing system as used herein includes but is not limited to one or more software modules, one or more hardware modules, one or more firmware modules, or combinations thereof, that work together to perform operations on electronic data. The physical layout of the modules may vary. A computing system may include multiple computing devices coupled via a network. A computing system may include a single computing device where internal modules (such as a memory and processor) work together to perform operations on electronic data. In some embodiments, a single computing system 200 includes the navigation software 100 and also includes one or both of: (A) all or a portion of the logical control layer 106; and (B) all or a portion of the physical control layer 108. On the other hand, in some embodiments, the logical control layer 106 and the physical control layer 108 are on one or more computing systems separate and distinct from the computing system 200 having the navigation software 100.

In some embodiments, the navigation software 100 executing on the computing system 200 interacts with the robot control server 102 and with the MRI System 104. The computing system 200 may use any suitable protocol(s), standard(s), data exchange format(s), or combination(s) of these, to communicate with and send/receive information to/from one or more of the systems described herein. The computing system 200 may send and receive information and requests using OpenIGTLink. The computing system 200 can receive, send, and store DICOM (Digital Imaging and Communications in Medicine) files and data. For example, the computing system 200 may receive a medical image from the MRI System 104. Additionally, the computing system 200 may send HTTP requests and provide HTTP responses. The responses may include Hyper Text Markup Language (HTML) files, or other suitable files, executable code, such as JAVASCRIPT, form elements, images, or other content. One or more elements of the content may be stored at the computing system 200. In some embodiments, the computing system 200 uses Simple Object Access Protocol (SOAP) to receive and send messages.

The computing system 200 includes one or more processor(s) 201, memory 202, storage 203, an input/output (I/O) interface 204, a communication interface 205, and a bus 206. The computing system 200 may take any suitable physical form. For example, and not by way of limitation, the computing system 200 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, PDA, a tablet computer system, one or more servers, a workstation, or a combination of two or more of these. In some embodiments, the computing system 200 is unitary. In some embodiments, the computing system 200 is distributed. The computing system 200 may span multiple locations. The computing system 200 may span multiple machines.

The processor(s) 201 include hardware for executing instructions, such as those making up a computer program. The processor(s) 201 may retrieve the instructions from the memory 202, the storage 203, an internal register, or an internal cache. The processor(s) 201 then decode and execute the instructions. Then, the processor(s) 201 write one or more results to the memory 202, the storage 203, the internal register, or the internal cache. The processor(s) 201 may provide the processing capability to execute the operating system, programs, user and application interfaces, and any other functions of the computing system 200.

The processor(s) 201 may include a central processing unit (CPU), one or more general-purpose microprocessor(s), application-specific microprocessor(s), and/or special purpose microprocessor(s), or some combination of such processing components. The processor(s) 201 may include one or more graphics processors, video processors, audio processors and/or related chip sets.

In some embodiments, the memory 202 includes main memory for storing instructions for the processor(s) 201 to execute or data for the processor(s) 201 to operate on. By way of example, the computing system 200 may load instructions from the storage 203 or another source to the memory 202. During or after execution of the instructions, the processor(s) 201 may write one or more results (which may be intermediate or final results) to the memory 202. One or more memory buses (which may each include an address bus and a data bus) may couple the processor(s) 201 to the memory 202. One or more memory management units (MMUs) may reside between the processor(s) 201 and the memory 202 and facilitate accesses to the memory 202 requested by the processor(s) 201. The memory 202 may include one or more memories. The memory 202 may be random access memory (RAM).

The storage 203 stores data and/or instructions. As an example and not by way of limitation, the storage 203 may include a hard disk drive, a floppy disk drive, flash memory, an optical disc, a magneto-optical disc, magnetic tape, or a Universal Serial Bus (USB) drive or a combination of two or more of these. In some embodiments, the storage 203 is a removable medium. In some embodiments, the storage 203 is a fixed medium. In some embodiments, the storage 203 is internal to the computing system 200. In some embodiments, the storage 203 is external to the computing system 200. In some embodiments, the storage 203 is non-volatile, solid-state memory. In some embodiments, the storage 203 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. The storage 203 may include one or more memory devices. The storage 203 may store application data, program modules and other information. One or more program modules stored in the storage 203 are configured to cause various operations and processes described herein to be executed. In some embodiments, the navigation software 100 resides on the storage 203 and executes on the computing system 200. The storage 203 may further store other programs and/or drivers that enable various functions of the computing system 200, graphical user interface (GUI) functions, and/or processor functions. The storage 203 may also store data files including, for example, image data, user data, configuration information, GUI components, such as graphical elements or templates, or other data required by the computing system 200.

The I/O interface 204 includes hardware, software, or both providing one or more interfaces for communication between the computing system 200 and one or more I/O devices. In some embodiments, the computing system 200 includes one or more I/O devices. One or more of these I/O devices may enable communication between a person and the computing system 200. By way of example and not by way of limitation, an I/O device may include a keyboard, keypad, microphone, monitor, mouse, touchpad, speaker, still camera, stylus, tablet, touch screen, trackball, video camera, another suitable I/O device or a combination of two or more of these. An I/O device may include one or more sensors. In some embodiments, the I/O interface 204 includes one or more device or software drivers enabling the processor(s) 201 to drive one or more of these I/O devices. The I/O interface 204 may include one or more I/O interfaces.

In some embodiments, the computing system 200 includes a display. For example, the display may be a liquid crystal display (LCD). In some embodiments, the navigation software 100 running on the computing system 200 presents GUI data on the display. In some embodiments, the GUI data is presented in conjunction with medical image data. Regarding outputting signals to the display, the processor(s) 201 rasterize an image to be displayed on the display, and transfer the rasterized image to the display via the I/O interface 204. The display then displays the image, such as a GUI. The processor(s) 201 are further operable to cause other types of images, such as medical images from the MRI System 104, to be displayed on the display. The computing system 200 may receive an input signal based on user inputs at the display. For example, in some embodiments, the display includes a touch sensitive element operable to receive user inputs or commands based on the touching one or more interface elements on the display. The interface element may be a graphical object presented on the display. A user may touch the touch sensitive display with a finger, stylus, or other tool to provide a user input. When the user touches a specific region on the touch sensitive display, the processor(s) 201 are notified via the I/O interface 204 of the coordinates of the region. The processor(s) 201 determine the content of a user input based on the notified coordinates and the display contents on the display, and execute processing based on them. In some embodiments, a mouse or touchpad is used in conjunction with information presented on the display to receive user inputs and selections. For example, a cursor may be used to select one or more interface elements presented in the GUI on the display. According to various embodiments, the touch sensitive display, the cursor, or other suitable method for providing an input, is used to specify one or more location(s) on a medical image presented in the GUI on the display to indicate, for example, a target and a planned insertion point for inserting a needle into a patient.

In some embodiments, the computing system 200 includes a keyboard/keypad. User inputs may also be provided via the keyboard/keypad. When the user presses a hard key of the keyboard/keypad, the processor(s) 201 are notified via the I/O interface 204 of information indicative of the user input. The processor(s) 201 execute processing based on the notification. The hard keys and/or buttons of the keyboard/keypad may be arranged in any suitable configuration. Furthermore, the input structures may include buttons, keys, switches, control pads, or other suitable structure, depending on specific implementation requirements.

The communication interface 205 includes hardware, software, or both providing one or more interfaces for communication (such as, for example, packet-based communication) between the computing system 200 and one or more other computing systems or one or more networks. As an example and not by way of limitation, the communication interface 205 may include a network interface card (NIC) or a network controller for communicating with an Ethernet or other wire-based network or a wireless NIC (WNIC) or wireless adapter for communicating with a wireless network, such as a WI-FI network. This disclosure contemplates any suitable network and any suitable communication interface 205 for it. As an example and not by way of limitation, the computing system 200 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the computing system 200 may communicate with a wireless PAN (WPAN) (such as, for example, a Bluetooth WPAN or an ultra-wideband (UWB) network), a WI-FI network, a WI-MAX network, a cellular telephone network (such as, for example, a Global System for Mobile Communications (GSM) network), or other suitable wireless network or a combination of two or more of these. The computing system 200 may include any suitable communication interface 205 for any of these networks, where appropriate. The communication interface 205 may include one or more communication interfaces 205.

The bus 206 interconnects various components of the computing system 200 thereby enabling the transmission of data and execution of various processes. The bus 206 may include one or more types of bus structures including a memory bus or memory controller, a peripheral bus, and a local bus using any of a variety of bus architectures.

III. Fiducial Frame

The fiducial frame contains a plurality of fiducial markers. The markers may all be the same shape and size, such as all being spherical markers, or the fiducial frame may contain fiducial markers having varying sizes and/or shapes. In some embodiments, the placement of the fiducial markers within the fiducial frame is in a ring shape. In some embodiments, the fiducial frame arranged in a ring shape includes the fiducial markers being are arranged asymmetrically. In some embodiments, all of the fiducial markers are in the same plane. There may be any suitable number of fiducial markers in the fiducial frame. For example, there may be 2 to 16 or more fiducial markers in the fiducial frame. In various embodiments, particularly where different shaped fiducial markers are used, a plurality of spherical fiducial markers is used. According to some embodiments, the fiducial frame includes at least three fiducial markers.

Figure 5:
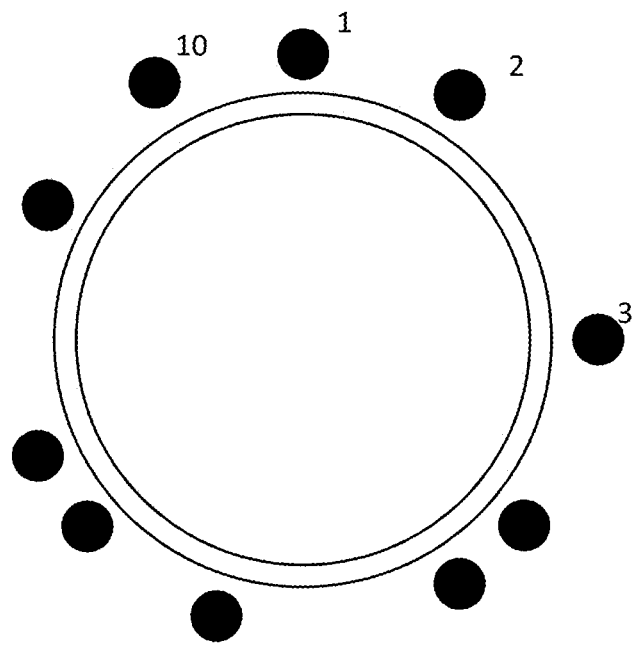
FIG. 5 shows an MR image of an example fiducial frame containing fiducial markers in accordance with some embodiments.

In some embodiments, a medical device may have multiple divots or holes that are either equally or randomly spaced around a ring or at each edge of the device. Then, when registration of the device is required, fiducial markers are placed in either the divots or holes (if holes, the fiducial marker may have a pin-shaped protrusion that fits into the hole; other formats of removable securing the fiducial markers to the medical device are also contemplated). The number of fiducial markers created can be defined based on the required quality of registration required for the particular application. FIG. 5 is an MR image of an example implementation of fiducial frame having a ring shape and asymmetrically arranged fiducial markers. The frame consists of 10 identical cylindrical liquid containers attached to a circular template; the template has 60 holes at every 6 degrees along a circle with a diameter of 110 mm allowing different configuration of markers. Each liquid container is fabricated by 3D printing, and has a spherical cavity with a diameter of 10 mm and filled with gadolinium-diethylenetriamine pentaacetic acid (Gd-DTPA) solution. Since the solution appears as a bright spherical object on T1-weighted MR images, the filled container works as a marker. As illustrated in FIG. 5, the MR image of the frame is along the plane parallel to the circle. The center points of the markers may be detected by the marker detection algorithm described herein.

In some embodiments, the fiducial frame includes fiducial markers to be used in conjunction with a CT scan. Fiducial markers used for CT scans may be any suitable fiducial marker enabling effective detection of the fiducial in the medical image generated by the CT scan. By way of example and not by way of limitation, fiducial markers used with CT scans may be polymers doped with barium sulfate, bismuth trioxide, bismuth subcarbonate, bismuth oxychloride, or tungsten. The configuration(s) of fiducial frames described and illustrated herein may be utilized for the fiducial markers used for CT scans. For example, some embodiments include a fiducial frame having fiducial markers to be used in conjunction with a CT scan, where the fiducial frame includes one or more of the following features: at least three fiducial markers in the fiducial frame; fiducial markers having a spherical shape; fiducial markers in a substantially planar arrangement; fiducial markers in a ring-shaped arrangement; fiducial markers in an asymmetrical arrangement.

Spherical Fiducial Markers

Figure 6:
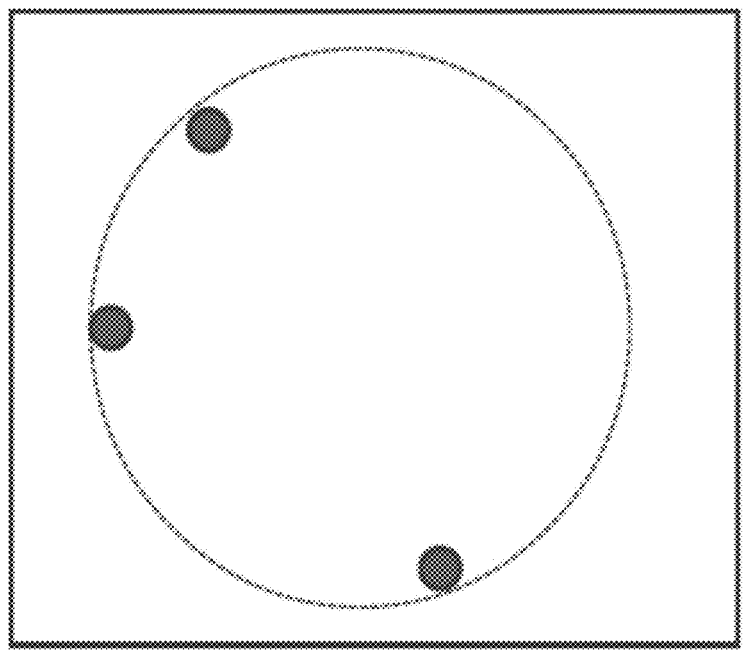
FIG. 6 illustrates a configuration of an example fiducial frame having a ring shape and asymmetrically arranged fiducial markers in accordance with some embodiments.

In some embodiments, the fiducial markers are spherical fiducial markers. In some embodiments, the detection algorithm relies on a spherical shape of individual fiducial marker with specific diameter $d_M$, and a circular configuration of the fiducial markers (e.g., ring-shaped). This is exemplified in FIG. 6. In FIG. 6, the example fiducial frame includes three spherical fiducial markers in a substantially planar arrangement. Furthermore, the fiducial markers of FIG. 6 are in a ring-shaped arrangement, where the arrangement of the fiducial markers is asymmetrical. The spherical shape image data can be detected easily by means of image processing. Also, spherical fiducial markers can be easily manufactured. Exemplary spherical fiducial markers are 3D-printed spherical liquid container filled with Gd-DTPA solution.

The spherical markers are aligned in a 2D circle with a predefined diameter $D_F$, but with irregular spacings so that the configuration is asymmetric, meaning that the fiducial frame does not look the same, even after rotating about the center and/or flipping the circle. Given the origin of the fiducial coordinate frame defined at the center of the circle, and its z-axis perpendicular to the circle, the coordinates of the i-th marker can be defined as follows:

$$x_i = \left(\frac{d_M}{2}\cos\theta_i, \frac{d_M}{2}\sin\theta_i, 0\right)(i=1, \ldots, N_M, \theta_1=0, \theta_{N_M}<2\pi)$$

where $N_M$ is the number of spherical markers.

A simple way to achieve the asymmetry requirement is to fulfill the following condition:

$\delta_i \neq \delta_j (0 \leq i < j \leq N_M)$ where $\delta_i$ is the angle between mark i and i+1 about the center of the circle:

$\delta_i = \theta_{i+1} - \theta_i$ ($1 \leq i < N_M - 1$)

$\delta_N = 2\pi - \theta_N$

While the fiducial markers for some embodiments are spherical, the term is not meant to imply a perfectly spherical form. Instead, the amount of error in the spherical shape should not be great enough to compromise the ability of the algorithms as described herein below to define the fiducial markers as having a spherical shape and applying an enhancement of the object.

IV. Cropping Process

Figure 7:
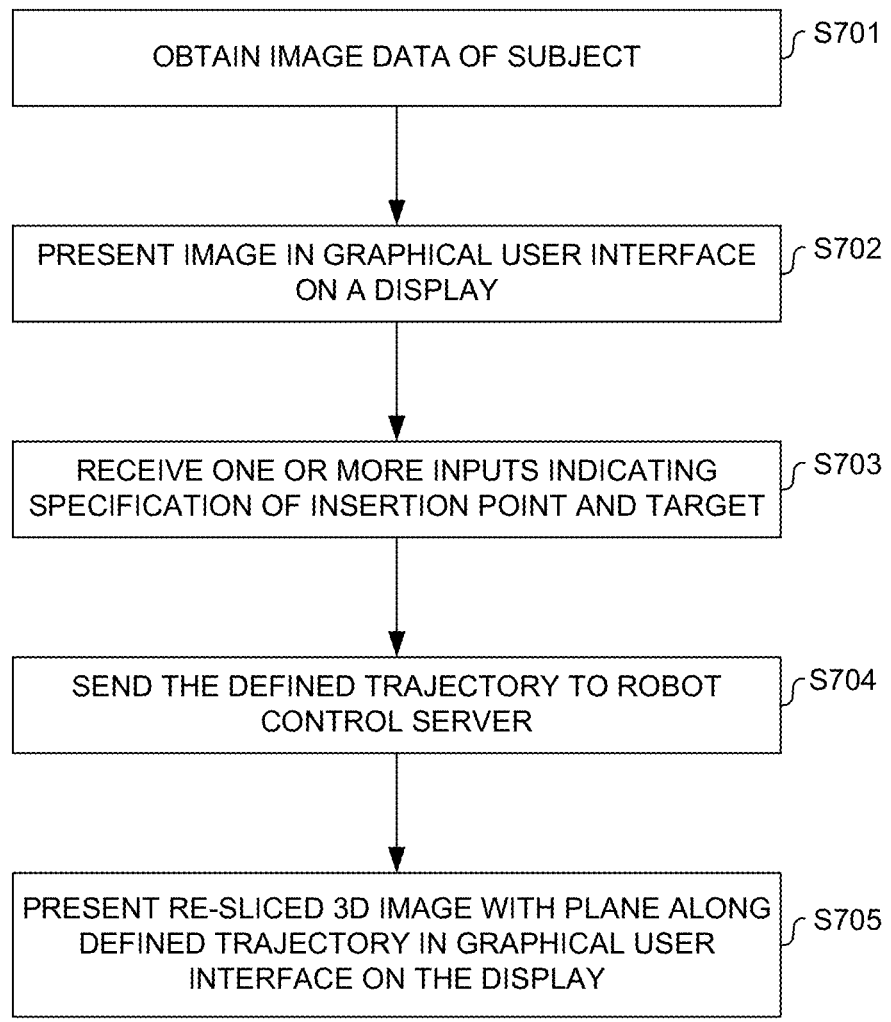
FIG. 7 is a flow diagram illustrating processing of image data in accordance with some embodiments.

In some embodiments, an automated image cropping process is performed using information associated with pre-procedure planning for a medical procedure. FIG. 7 illustrates an example flow of operations at the computing system 200 running the navigation software 100. In some embodiments, operations illustrated in FIG. 7 are carried out based on information associated with pre-procedure planning.

In step S701, the computing system 200 obtains image data of a subject. For example, the image data may be medical image data of a patient's anatomy. In some embodiments, the image data includes MRI data. For example, while a patient is in the gantry of an MRI scanner, the MRI scanner scans at least a portion of the patient's body. Based on the scan, the MRI scanner generates an image of the patient's anatomy and the MRI system 104 sends 3D image data of the patient's anatomy to the computing system 200. In some embodiments, the image data includes CT data. For example, a CT scan of a portion of a patient's body may be taken and the image data generated based on the CT scan. After the image data is generated, the imaging system sends the image data to the computing system 200.

In some embodiments, the computing system 200 obtains the image data as a file from a source other than the imaging system that generated the image data. For example, the computing system 200 may read or retrieve the file from a storage device, such as a USB flash drive connected to the computing system 200, or any other suitable storage medium accessible to the computing system 200. In some embodiments, the computing system 200 obtains the image data from a computing system that transmits the image data file over a network, such as a LAN, WAN, other suitable network, or combination of networks.

The navigation software 100 executing on the computing system 200 thus obtains the image data at the computing system 200 from, for example, the imaging system which generated the image data, or from a storage medium, or from another computing system over a network.

In step S702, the navigation software 100 executing on the computing system 200 presents the image data, obtained in step S701, in a GUI on a display. In some embodiments, the computing system 200 includes a display, and the image data is presented in a GUI on the display of the computing system 200. In some embodiments, the display is an output device and the navigation software 100 executing on the computing system 200 outputs the image data to the display via the I/O interface 204. In some embodiments, step S702 includes presentation of a medical image in a GUI, the medical image including a 3D representation of the patient's anatomy. The medical image presented in the GUI may be used as a planning image for pre-procedure planning of a medical procedure. For example, the navigation software 100 executing on the computing system 200 provides a GUI including interface elements and features which enable a user, such as a doctor, to provide inputs via the GUI to specify one or more location(s) on the medical image presented in the GUI. In some embodiments, the GUI displays a section of the planning image along any plane and allows the physician to specify targets and skin entry points. Accordingly, a physician can define a trajectory of needle placement by specifying the targets and skin entry point on the planning image.

In step S703, the computing system 200 receives one or more input(s) indicating the specification of an insertion point and a target on the medical image. In some embodiments, step S703 includes receiving the input(s) while the medical image is presented in the GUI on the display. The input(s) may be received in any suitable manner. By way of example and not by way of limitation, a user may provide one or more input(s) specifying the insertion point and the target on the medical image by one or more of the following: touching a touch sensitive display with a finger, stylus, or other tool; controlling a cursor with a mouse or touchpad; pressing a key, button, or other input structure; manipulating or selecting one or more interface elements included in the GUI; another technique for providing an input; or a combination of two or more of these. The planned insertion point is a skin entry point at which a needle is to be inserted into the patient's body. The target is the location, spot or area to be treated and/or the anatomy to be accessed. The trajectory of needle placement is defined by connecting the planned insertion point and the target.

In step S704, the navigation software 100 executing on the computing system sends the defined trajectory to the robot control server 102. In some embodiments, step S704 includes sending information indicating the target and the planned insertion point. For example, according to some embodiments, the robot control server 102 uses the target and insertion point information to determine the trajectory at the robot control server 102. In some embodiments, step S704 includes the navigation software 100 determining the trajectory of needle placement by connecting the planned insertion point and the target. Then, the navigation software 100 transfers to the robot control server 102 the defined trajectory.

In step S705, the navigation software 100 executing on the computing system 200 may present a re-sliced 3D image with plane along defined trajectory in the GUI on the display. For example, once the trajectory has been defined, the navigation software 100 can re-slice the 3D image with a plane along the trajectory so that the physician can find any critical structures and obstacles around the path. By way of example, FIG. 3 shows a medical image presented on an example graphical user interface of the navigation software 100. The image includes a 3D representation of patient anatomy and information identifying a planned trajectory and target, and the image is sliced with plane along the defined trajectory.

Figure 8:
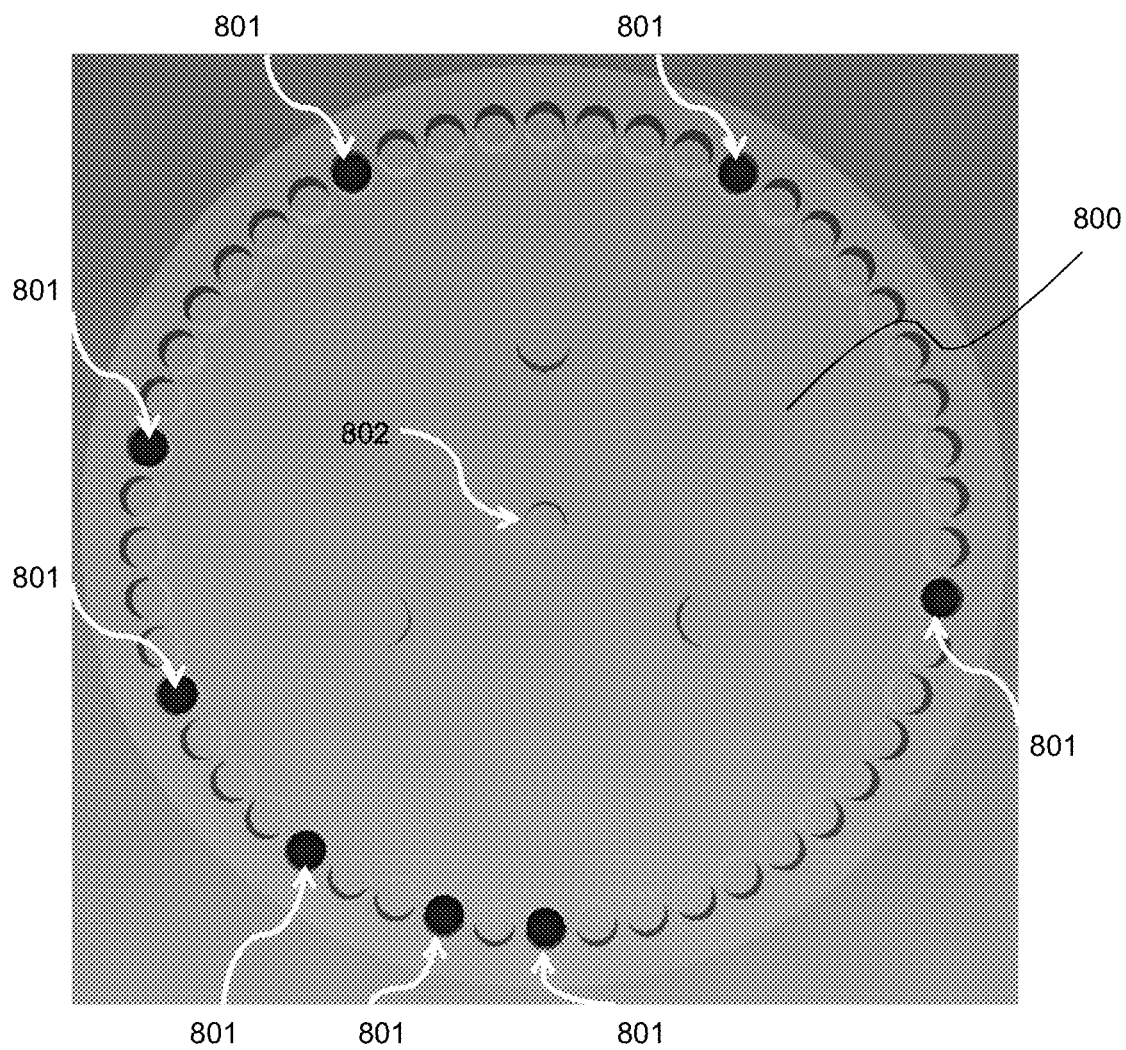
FIG. 8 illustrates an example medical device including fiducial markers in accordance with some embodiments.

A medical device may then be placed or secured onto a patient over a surgical site. FIG. 8 illustrates an example medical device 800 including fiducial markers in accordance with some embodiments. FIG. 8 depicts a medical device to be registered 800 with eight fiducial markers 801 arranged asymmetrically on a single plane in a circular layout. By arranging the fiducial markers on a single plane the footprint for cropping for registration is minimized. Moreover, the asymmetric layout of the fiducial markers 801 guarantees the true orientation of the medical device 800 in the medical images can be determined. The fiducial markers 801 may be a fiducial marker as described above and the fiducial frame may be arranged in a manner described herein. Located at the center of the medical device 800 is a physical needle insertion point 802 through which a needle, probe or other device is inserted after the medical device 800 has been positioned. Next, medical image data 1005 is obtained of the medical device 800 and the patient. This image data 1005 is, for example, MRI or CT data. The fiducial markers 801 may appear as fiducial marker objects in the medical image. In some embodiments, the medical image may be a calibration image sent to the computing system 200 in order to perform registration of the medical device 800.

Figure 9:
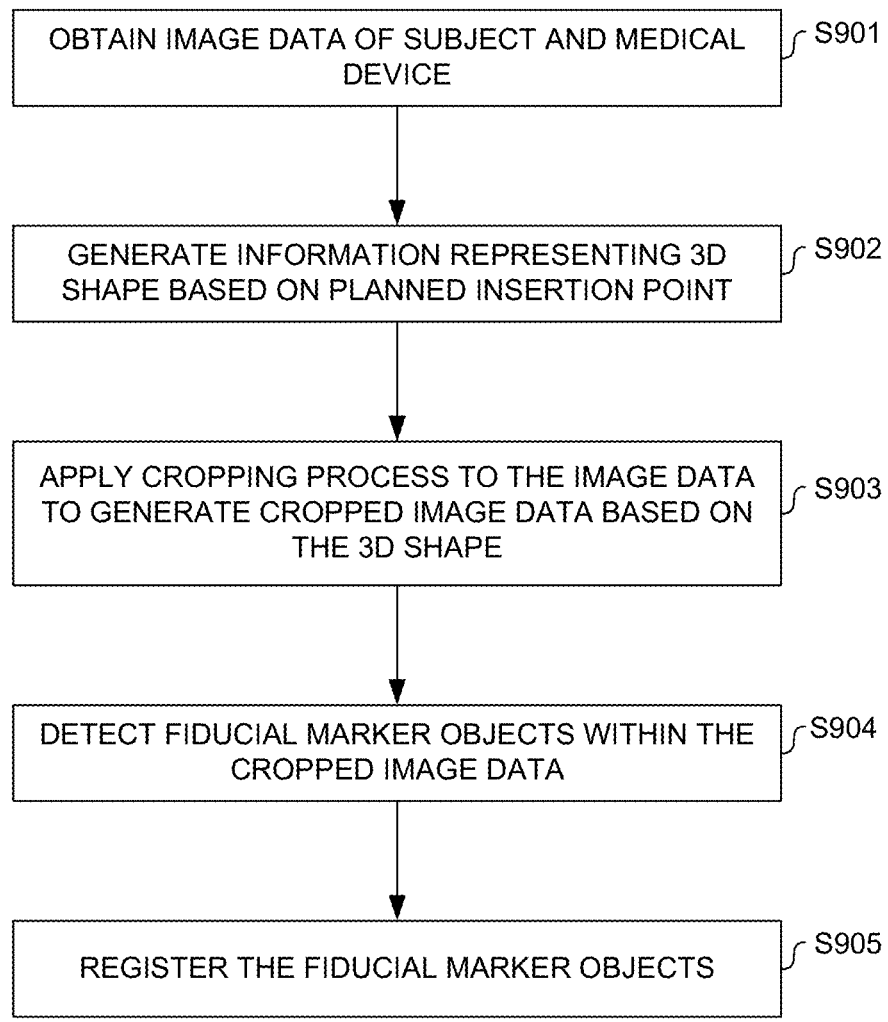
FIG. 9 is a flow diagram illustrating a process of cropping image data in accordance with some embodiments.

FIG. 9 illustrates an example flow of operations at the computing system 200 running the navigation software 100. In some embodiments, operations described with respect to FIG. 9 are carried out when a calibration image is obtained from the MRI System 104. The operations of FIG. 9 are described with reference to FIGS. 10(A)-10(C).

In step S901, the computing system 200 obtains image data of a subject and a medical device. In some embodiments, step S901 includes obtaining image data of a subject and a medical device where the medical device includes fiducial markers and the image data includes three-dimensional image data. For example, the image data may be medical image data of the patient's anatomy of FIG. 7 and the medical device 800. In some embodiments, the image data includes MRI data. For example, while a patient is in the gantry of an MRI scanner, the MRI scanner scans at least a portion of the patient's body while the medical device 800 is positioned thereon. Based on the scan, the MRI scanner generates an image of the patient's anatomy and the medical device 800, and the MRI system 104 sends 3D image data of the patient's anatomy and medical device 800 to the computing system 200. In some embodiments, the image data includes CT data. For example, a CT scan of a portion of a patient's body and the medical device 800 may be taken and the image data generated based on the CT scan. After the image data is generated, the imaging system sends the image data to the computing system 200.

In some embodiments, the computing system 200 obtains the image data as a file from a source other than the imaging system that generated the image data. For example, the computing system 200 may read or retrieve the file from a storage device, such as a USB flash drive connected to the computing system 200, or any other suitable storage medium accessible to the computing system 200. In some embodiments, the computing system 200 obtains the image data from a computing system that transmits the image data file over a network, such as a LAN, WAN, other suitable network, or combination of networks.

The navigation software 100 executing on the computing system 200 thus obtains the image data of the patient and medical device 800 at the computing system 200 from, for example, the imaging system which generated the image data, or from a storage medium, or from another computing system over a network.

In step S902, the navigation software 100 executing on the computing system 200 generates information representing a 3-dimensional shape based on a planned insertion point. In step S903, the navigation software 100 executing on the computing system 200 applies a cropping process to the image data obtained in step S901 based on the 3-dimensional shape generated in step S902. Steps S902 and S903 are described with reference to FIGS. 10(A)-10(C).

FIG. 10(A) depicts an example medical image dataset 1005 in which automated cropping will be performed. Although the medical image dataset 1005 is shown in 2-dimensions, the dataset is a standard 3D medical imaging dataset and automated cropping will be performed in 3-dimensions. A metallic artifact in a medical image from the patient bed 1006 is depicted. These artifacts are often mistaken as a fiducial marker when the image is not pre-cropped before performing automatic registration. During pre-procedure planning the user selects a planned needle insertion point 1001 using the standard clinical pre-procedure planning workflow. Automatic image cropping is performed by constructing a spherical area 1002 in the 3D image set. The size of the spherical area 1002 is set to the maximum size of the medical device 800 to be registered plus the expected maximum error between the physician's physical placement of the medical device 800 on the patient versus the planned insertion point 1001. A 3-dimensional representation of the spherical area 1008 is shown in FIG. 10(B) for reiteration and clarity of cropping in 3-dimensions (not just 2-dimensions). An image cropping cube 1003 is computed which fully encloses the spherical area 1002 as shown in the 3-dimensional view of the image cropping cube 1009. The image cropping cube 1003 is then used to crop the image dataset leading to a cropped image 1007 (FIG. 10(C)). The cropped image dataset 1007 is then searched for fiducial marker objects 1004. In some embodiments, the cropped image data set 1007 includes at least two fiducial markers.

According to various embodiments described herein, the error information may be information that is a predetermined value. For example, the amount of error used in various embodiments described herein may be a value determined prior to automatic registration and pre-programmed into the navigation software 100. In some embodiments, the error is defined as a percentage of a size of the medical device 800. Any suitable method for determining the amount of error to be included may be utilized.

In step S904, the navigation software 100 executing on the computing system 200 detects fiducial marker objects 1004 within the cropped image data 1007. Detection of fiducial marker objects within image data may be performed in any suitable manner. The detection of fiducial marker objects is discussed further in a section below.

In step S905, the navigation software 100 executing on the computing system 200 registers the fiducial marker objects 1004 detected in step S904. Registration of fiducial marker objects may be performed in any suitable manner. The registration of fiducial marker objects is discussed further in a section below.

Figure 11:
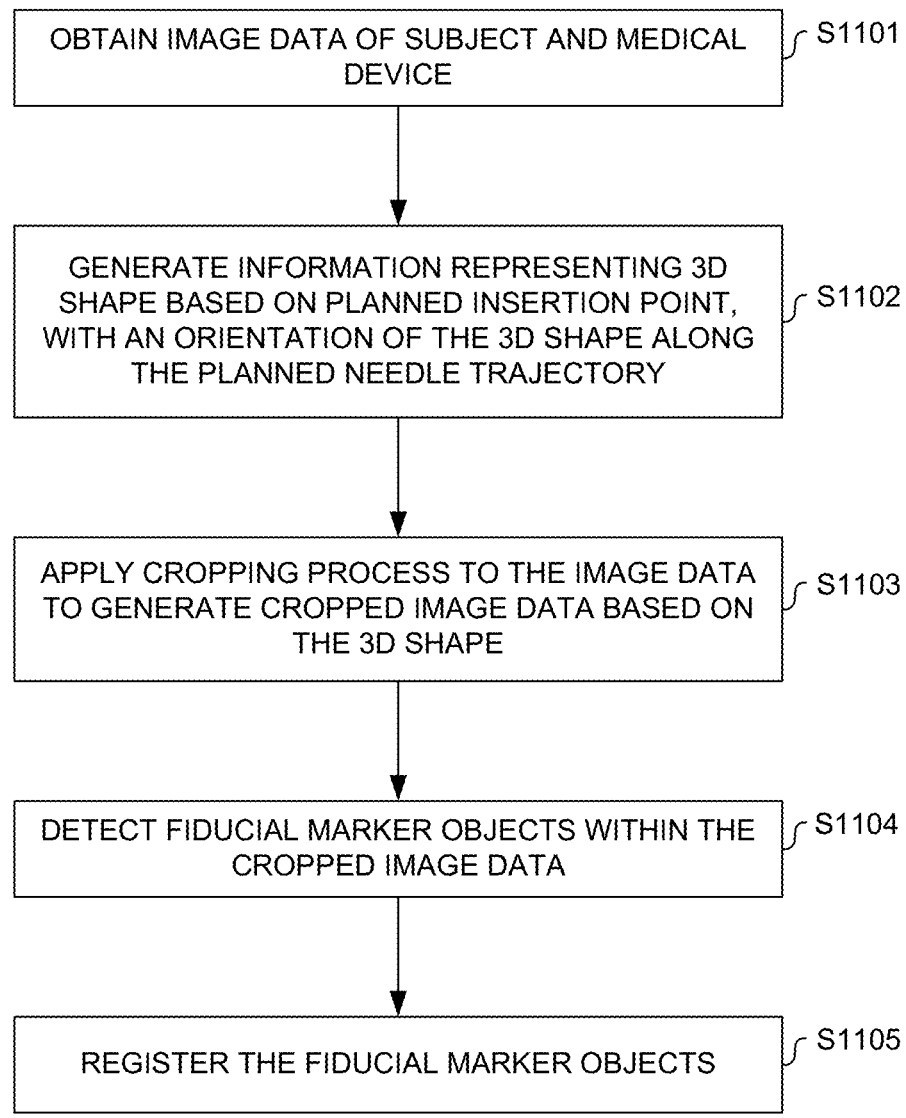
FIG. 11 is a flow diagram illustrating a process of cropping image data in accordance with some embodiments.

FIG. 11 illustrates an example flow of operations at the computing system 200 running the navigation software 100. In some embodiments, operations described with respect to FIG. 11 are carried out when a calibration image is obtained from the MRI System 104. The operations of FIG. 11 are described with reference to FIGS. 12(A)-12(C).

In step S1101, operations are carried out in a manner corresponding to step S901 described above. In step S1102, the navigation software 100 executing on the computing system 200 generates information representing a 3-dimensional shape based on a planned insertion point, with an orientation of the 3-dimensional shape along the planned needle trajectory. In step S1103, the navigation software 100 executing on the computing system 200 applies a cropping process to the image data obtained in step S1101 based on the 3-dimensional shape generated in step S1102. Steps S1102 and S1103 are described with reference to FIG. 12(A)-12(C).

FIG. 12(A) depicts the example medical image dataset 1005 in which automated cropping will be performed. During pre-procedure planning the user selects a planned needle insertion point 1001 using the standard clinical pre-procedure planning workflow. During pre-procedure planning the user selects a planned needle target 1203. A planned needle trajectory 1202 is then automatically defined connecting the planned needle insertion point 1001 and the planned needle target 1203. An image cropping rectangular cube 1201 is constructed and oriented along the planned needle trajectory 1202 in order to crop the medical image dataset 1005. A 3-dimensional representation of the image cropping rectangular cube 1208 is shown (FIG. 12(B) for reiteration and clarity of cropping in 3-dimensions (not just 2-dimensions). The length of the image cropping rectangular cube 1207 and the depth of the image cropping rectangular cube 1205 are set to the maximum length and depth, respectively, of the medical device 800 to be registered once placed on the patient plus some error margin. The error margin is set to the expected maximum Eigenvector distance between the physician's physical placement of the medical device 800 on the patient and the planned insertion point 1001. The height of the image cropping rectangular cube 1206 is set to the maximum distance from the medical device 800 base plane placed on the patient and the fiducial markers 801 in the medical device 800 plus some error margin. The error margin is set to the expected maximum displacement of the medical device 800 due to patient breathing or the expected maximum tilt of the medical device 800 once placed on the patient whichever is higher.

After cropping the original medical image dataset 1005 using the image cropping rectangular cube 1201 a smaller cropped image dataset 1204 is obtained (FIG. 12(C). This cropped image dataset is then searched for fiducial marker objects 1004. FIG. 12(C) depicts an actual cropping of the image which is one method of limiting the fiducial search area, but the image cropping rectangular cube 1201 could instead be used simply as a fiducial search box without actually cropping the image. More specifically, the entire example medical image dataset 1005 could be searched for fiducials and only fiducials found within the image cropping rectangular cube 1201 would be considered valid fiducials. Actually cropping the image does, however, limit the searchable area and thus speed up the registration algorithms.

In step S1104, the navigation software 100 executing on the computing system 200 detects fiducial marker objects 1004 within the cropped image data 1204. Detection of fiducial marker objects within image data may be performed in any suitable manner. The detection of fiducial marker objects is discussed further in a section below.

In step S1105, the navigation software 100 executing on the computing system 200 registers the fiducial marker objects 1004 detected in step S1104. Registration of fiducial marker objects may be performed in any suitable manner. The registration of fiducial marker objects is discussed further in a section below.

Figure 13:
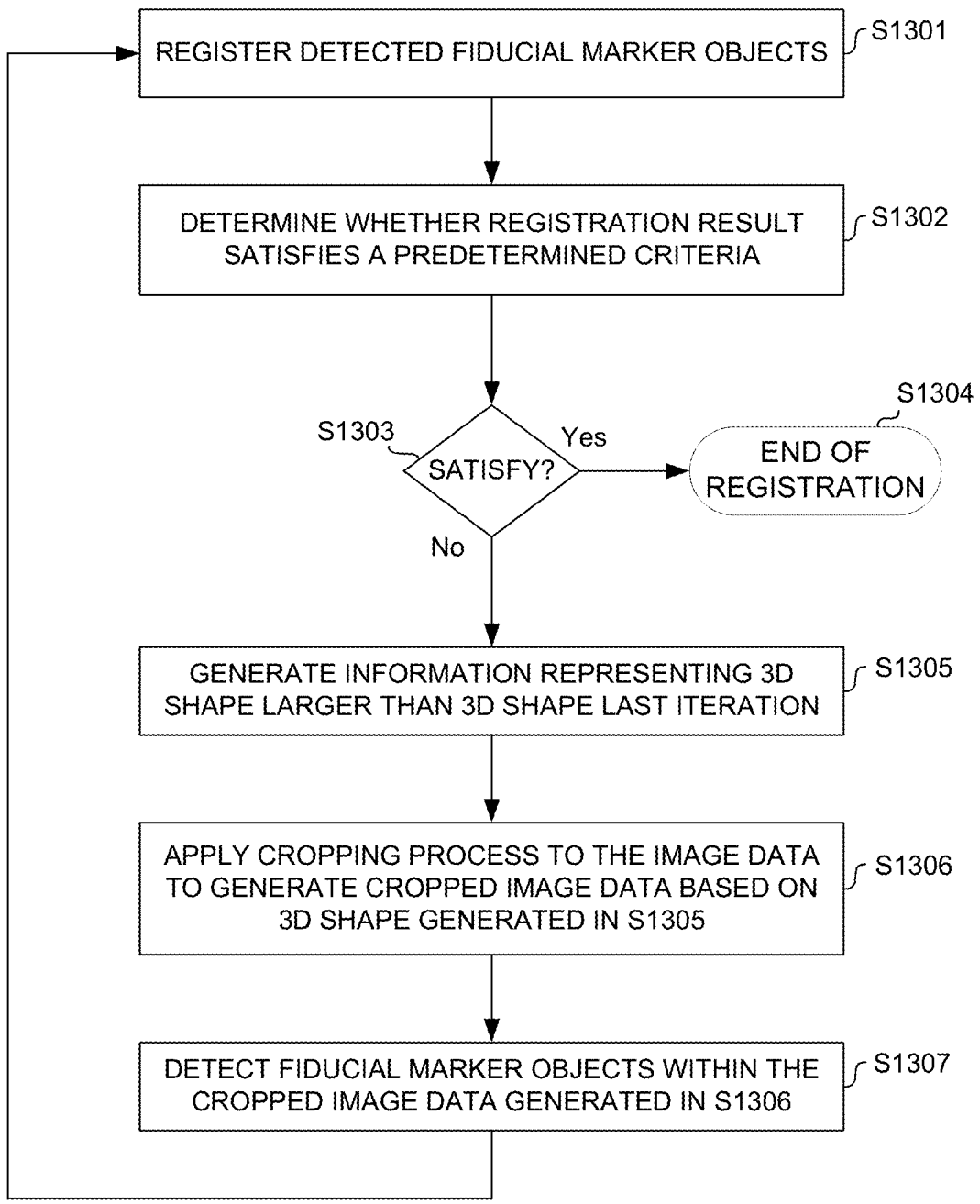
FIG. 13 is a flow diagram illustrating a process of cropping image data in accordance with some embodiments.

FIG. 13 illustrates an example flow of operations at the computing system 200 running the navigation software 100. In some embodiments, operations described with respect to FIG. 13 are carried out after a process according to FIG. 11, for example, is carried out. The operations of FIG. 13 are described with reference to FIGS. 14(A)-14(C).

FIG. 14(A) depicts the medical image dataset 1005 in which automated cropping will be performed. During pre-procedure planning the user selects a planned needle insertion point 1001 using the standard clinical pre-procedure planning workflow. During pre-procedure planning the user selects a planned needle target 1203 using the standard clinical pre-procedure planning workflow. A planned needle trajectory 1202 is then automatically defined connecting the planned needle insertion point 1001 and the planned needle target 1203. Three iterations—image cropping rectangular cube iteration A 1401, image cropping rectangular cube iteration B 1402, and image cropping rectangular cube iteration C 1403—are constructed along the planned needle trajectory 1202 in order to iteratively crop the medical image dataset 1005 (FIG. 14(B)). The image cropping rectangular cubes A 1401, B 1402 and C 1403 are centered around the planned needle insertion point 1001 (FIG. 14(C)). A 3-dimensional representation of the image cropping rectangular cube iteration A 1407, 3-dimensional representation of the image cropping rectangular cube iteration B 1408, and 3-dimensional representation of the image cropping rectangular cube iteration C 1409 are shown for reiteration and clarity of cropping in 3-dimensions (not just 2-dimensions). The iteration process is intended to narrow the cropped image area by iteratively expanding the cropped image area until the optimal registration result is achieved (steps S1302, S1303, S1304). The iteration process allows for identification of the smallest cropped area that still contains all fiducial markers. Determining in step S1302 whether the registration result satisfies predetermined criteria (Yes or No in step S1303) may be based upon any suitable criteria. For example, the criteria may be a predetermined amount or percentage of fiducial markers found. If so, then registration ends in step S1304. If the criteria is not satisfied, then the iterative process continues. According to some embodiments, an iteration process is carried out by iteratively shrinking, rather than expanding, the cropped image area until the optimal registration result(s) is/are achieved. For example, incremental shrinking of the cropped image area centered on the planned needle insertion point 1001 may be carried out. The cropped image area may shrink to a predetermined size or by a predetermined percentage with successive iterations. The process may continue until a predetermined result—for example, a predetermined amount or percentage of fiducial markers found—is achieved.

Regarding iteration A, length 1410 and depth 1411 of the image cropping rectangular box iteration A 1407 are equal to the expected minimum error between the physician's physical placement of the medical device 800 on the patient versus the planned insertion point 1001. The height 1412 of the image cropping rectangular box iteration A 1407 is set to the expected minimum displacement of the medical device 800 due to patient breathing or the expected minimum tilt of the medical device 800 once placed on the patient whichever is higher. The resulting 3-dimensional Cropped Image Dataset Iteration A is given by 1404 (FIG. 14(C)). Automatic registration is then performed (step S1301) on this dataset by searching for fiducial marker objects 1004.

Regarding iteration B, length 1413 and depth 1414 of the image cropping rectangular box iteration B 1408 are equal to the length 1410 and depth 1411 of the image cropping rectangular box iteration A 1407 plus a small error margin. The height 1415 of the image cropping rectangular box iteration B 1408 is set to height 1412 of image cropping rectangular box iteration A 1407 plus a large error margin (step S1305). The resulting 3-dimensional Cropped Image Dataset Iteration B is given by 1405 (step S1306). Automatic registration is then performed on this dataset by searching for fiducial marker objects 1004 (step S1307).

Regarding iteration C, length 1416 and depth 1417 of the image cropping rectangular box iteration C 1409 is equal to the length 1410 and depth 1411 of the image cropping rectangular box iteration A 1407 plus a large error margin. The height 1418 of the image cropping rectangular box iteration C 1409 is set to height 1415 of image cropping rectangular box iteration B 1408. The resulting 3-dimensional Cropped Image Dataset Iteration C is given by 1406. Automatic registration is then performed on this dataset by searching for fiducial marker objects 1004.

If a fourth cropping (Iteration D) is needed, then the length, depth, and height of the image cropping rectangular box iteration D will be set based on the registration results that iteration B and iteration C yielded. For example, if iteration B found six of eight fiducials and iteration C again found only six of eight fiducials, then the height of the image cropping rectangular box iteration D will be expanded further in an attempt to find the remaining two fiducials. Automatic registration is then performed on this dataset by searching for fiducial marker objects 1004.

Figure 15:
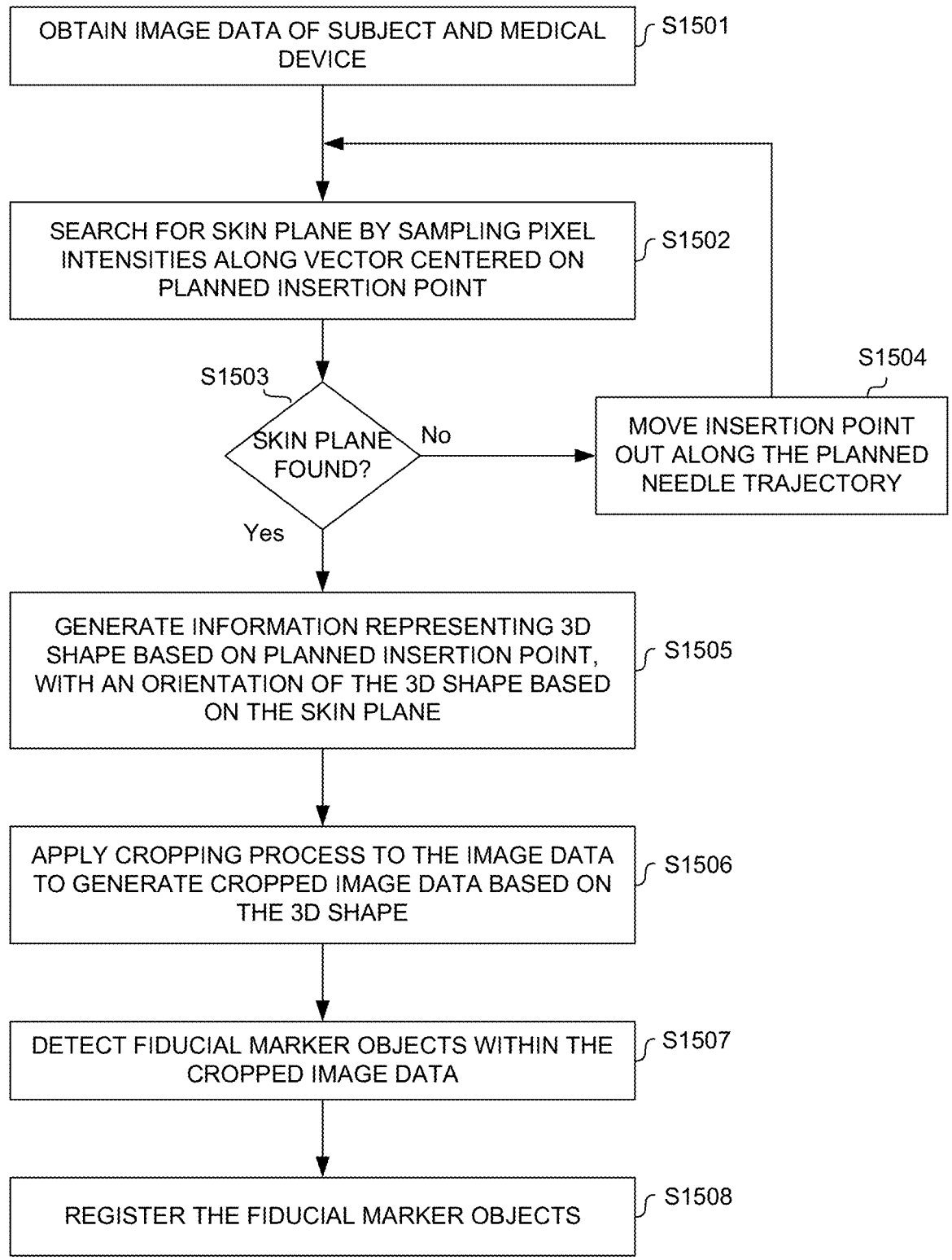
FIG. 15 is a flow diagram illustrating a process of cropping image data in accordance with some embodiments.

FIG. 15 illustrates an example flow of operations at the computing system 200 running the navigation software 100. In some embodiments, operations described with respect to FIG. 15 are carried out when a calibration image is obtained from the MRI System 104. The operations of FIG. 15 are described with reference to FIG. 16.

In step S1501, operations are carried out in a manner corresponding to step S901 described above. In step S1502, the navigation software 100 executing on the computing system 200 searches for a skin plane by sampling pixel intensities along a vector centered on the planned insertion point. If the skin plane is not found (no in step S1503), the insertion point is moved out along the planned needle trajectory (step S1504). If the skin plane is found (yes in step S1503), the process advances to step S1505, in which the navigation software 100 generates information representing a 3-dimensional shape based on a planned insertion point, with an orientation of the 3-dimensional shape based on the skin plane. In step S1506, the navigation software 100 executing on the computing system 200 applies a cropping process to the image data obtained in step S1501 based on the 3-dimensional shape generated in step S1505. The steps S1502-S1506 are described with reference to FIGS. 16(A)-16(C).

FIG. 16(A) depicts the medical image dataset 1005 in which automated cropping will be performed. During pre-procedure planning the user selects a planned needle insertion point 1001 using the standard clinical pre-procedure planning workflow. During pre-procedure planning the user selects a planned needle target 1203 using the standard clinical pre-procedure planning workflow. A planned needle trajectory 1202 is then automatically defined connecting the planned needle insertion point 1001 and the planned needle target 1203. Pixel intensity sampling is performed along a vector centered on the planned needle insertion point 1001. The pixel intensity sampling vector is rotated around the planned needle insertion point 1001 in order to find the skin plane 1602. At each orientation of the Skin Plane Sampling Vector A 1603, Skin Plane Sampling Vector B 1604, and so on, the intensity of each pixel along the vector is sampled. The skin plane 1602 is determined when all of the sampled pixel intensities are near the Hounsfield unit (HU) of air, namely, near a value of −1,000 HU. It is possible that the planned needle insertion point 1001 is selected within the body rather than in the air directly next to the body. When this occurs, no skin plane can be found since no rotation of the intensity sampling vector yields intensities close to the Hounsfield unit of air. If no skin plane 1602 is found, the algorithm will move the planned insertion point further away from the planned needle target 1203 along the planned needle trajectory 1202 and again sample pixel intensities along a rotating vector centered on the new planned needle insertion point 1001 to find the skin plane 1602. This process repeats until the skin plane is identified.

An image cropping rectangular cube 1601 is constructed oriented with the found skin plane 1602 in order to crop the medical image dataset 1005. A 3-dimensional representation of the image cropping rectangular cube 1609 is shown in FIG. 16(B) for reiteration and clarity of cropping in 3-dimensions (not just 2-dimensions). The length 1608 of the image cropping rectangular cube 1609 and the depth 1606 of the image cropping rectangular cube 1609 are set to the maximum length and depth, respectively, of the medical device 800 to be registered once placed on the patient plus some error margin. The error margin is set to the expected maximum error between the physician's physical placement of the medical device 800 on the patient versus the planned insertion point 1001. The height 1607 of the image cropping rectangular cube 1609 is set to the maximum height of the fiducial markers 801 in the medical device 800 from the medical device 800 plane placed on the patient plus some error margin. The error margin is set to the expected maximum displacement of the medical device 800 due to patient breathing or the expected maximum tilt of the medical device 800 once placed on the patient whichever is higher. After cropping the original medical image dataset 1005 using the image cropping rectangular cube 1601 a smaller cropped image dataset 1605 is obtained (FIG. 16(C)). This cropped image dataset is then searched for fiducial marker objects 1004.

In step S1507, the navigation software 100 executing on the computing system 200 detects fiducial marker objects 1004 within the cropped image data 1605. Detection of fiducial marker objects within image data may be performed in any suitable manner. The detection of fiducial marker objects is discussed further in a section below.

In step S1508, the navigation software 100 executing on the computing system 200 registers the fiducial marker objects 1004 detected in step S1507. Registration of fiducial marker objects may be performed in any suitable manner. The registration of fiducial marker objects is discussed further in a section below.

Figure 17:
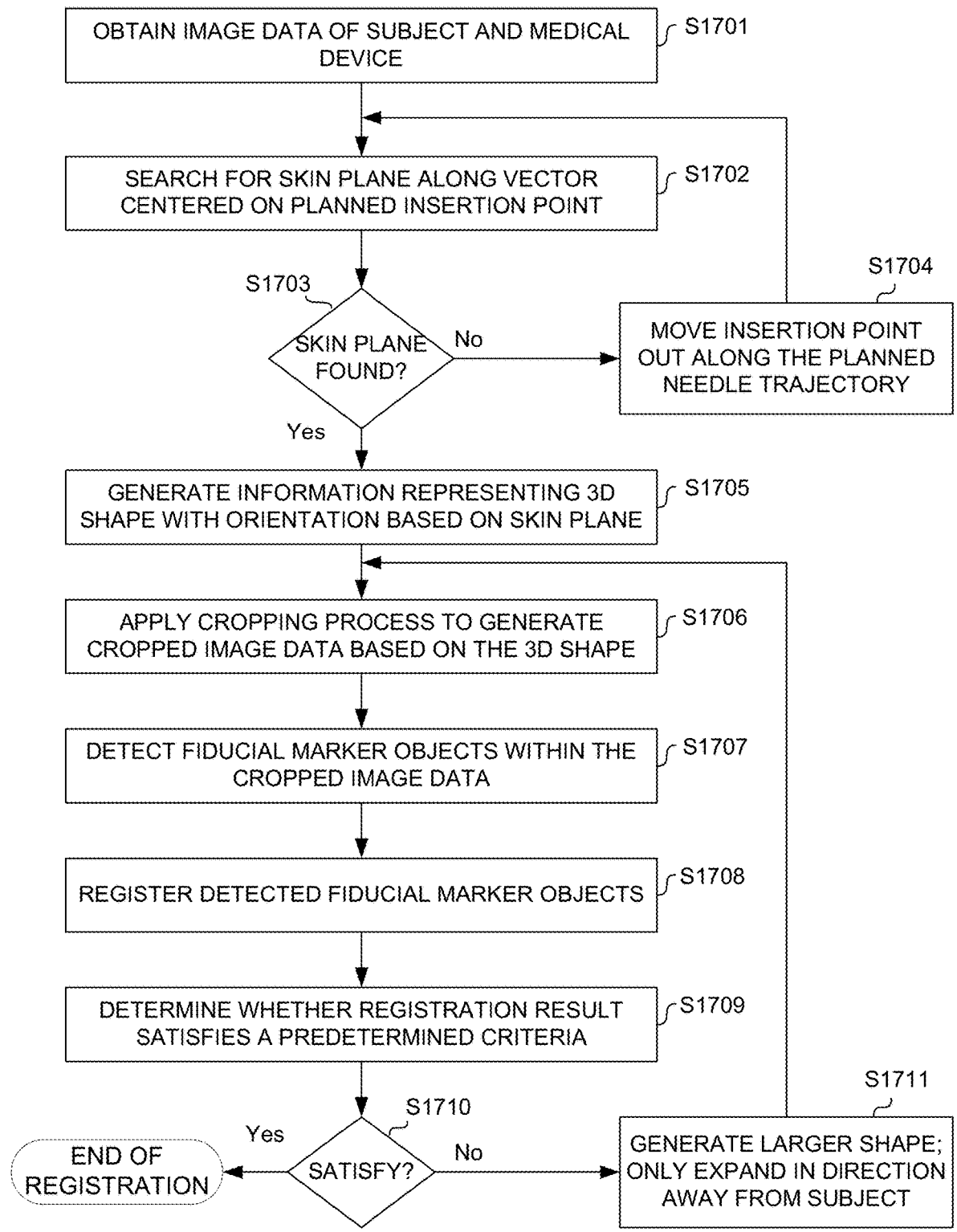
FIG. 17 is a flow diagram illustrating a process of cropping image data in accordance with some embodiments.

FIG. 17 illustrates an example flow of operations at the computing system 200 running the navigation software 100. In some embodiments, operations described with respect to FIG. 17 are carried out when a calibration image is obtained from the MRI System 104. FIG. 17 comprises a combination of the method of FIG. 13 and the method of FIG. 15, and is described with reference to FIGS. 18(A)-18(C).

FIG. 18(A) depicts the medical image dataset 1005 in which automated cropping will be performed (obtained in step S1701). During pre-procedure planning the user selects a planned needle insertion point 1001 using the standard clinical pre-procedure planning workflow. During pre-procedure planning the user selects a planned needle target 1203 using the standard clinical pre-procedure planning workflow. A planned needle trajectory 1202 is then automatically defined connecting the planned needle insertion point 1001 and the planned needle target 1203. Pixel intensity sampling is performed along a vector centered on the planned needle insertion point 1001. The pixel intensity sampling vector is rotated around the planned needle insertion point 1001 in order to find the skin plane 1602 (S1702). At each orientation of the skin plane sampling vector A 1603, skin plane sampling vector B 1604, and so on, the intensity of each pixel along the vector is sampled. The skin plane 1602 is determined when all of the sampled pixel intensities are near the Hounsfield unit of air, as described with reference to FIGS. 16(A)-16(C). It is possible that the planned needle insertion point 1001 is selected within the body rather than in the air directly next to the body. When this occurs, no skin plane can be found since no rotation of the intensity sampling vector yields intensities close to the Hounsfield unit of air (no in step S1703). If no skin plane 1602 is found, the algorithm will move the planned insertion point further away from the planned needle target 1203 along the planned needle trajectory 1202 and again sample pixel intensities along a rotating vector centered on the new planned needle insertion point 1001 to find the skin plane 1602 (S1704). This process repeats until the skin plane is identified (yes in step S1703).

Three iterations—image cropping rectangular cube iteration A 1802, image cropping rectangular cube iteration B 1801, and image cropping rectangular cube iteration C 1803—are constructed oriented parallel with the skin plane 1602 in order to iteratively crop the medical image dataset 1005. Since the skin plane 1602 has been identified, the bottom edge of the cropping boxes 1816 could be set to the same as the skin plane 1602. However, since registration has not yet been performed, the skin plane 1602 is only an estimate of the medical device 800 plane, and in actuality the medical device 800 could be tilted due to curvature of the patient. Therefore, the bottom edge of the cropping boxes 1816 should be set to a preset distance below the insertion point 1001 to correct for any error between skin plane 1602 and the physical medical device 800 plane. The iterations of cropping should only expand the height (e.g., height 508, height 511, height 514) of the cropping box away from the patient rather than down into the patient anatomy since the fiducial marker objects 1004 are known to be outside the patient's body. A 3-dimensional representation of the image cropping rectangular cube iteration A 1817, 3-dimensional representation of the image cropping rectangular cube iteration B 1818, and 3-dimensional representation of the image cropping rectangular cube iteration C 1819 are shown in FIG. 18(B) for reiteration and clarity of cropping in 3-dimensions (not just 2-dimensions) (step S1705). The iteration process is intended to narrow the cropped image area by iteratively expanding the cropped image area until the optimal registration result is achieved (step S1706, step S1709, S1710 and S1711). The iteration process allows for identification of the smallest cropped area that still contains all fiducial markers (S1710, FIG. 18(C)).

Regarding iteration A, length 1807 and depth 1809 of the image cropping rectangular cube iteration A 1817 are equal to the expected minimum error between the physician's physical placement of the medical device 800 on the patient versus the planned insertion point 1001. The height 1808 of the image cropping rectangular cube iteration A 1817 is set to the expected minimum displacement of the device due to patient breathing or the expected minimum tilt of the medical device 800 once placed on the patient whichever is higher. The resulting 3-dimensional cropped image dataset iteration A is given by 1804 (FIG. 18(C)). Automatic registration is then performed on this dataset by searching for fiducial marker objects 1004 (steps S1707 and S1708).

Regarding iteration B, length 1810 and depth 1812 of the image cropping rectangular cube iteration B 1818 are equal to the length 1807 and depth 1809 of the image cropping rectangular cube iteration A 1817 plus a small error margin. The height 1811 of the image cropping rectangular cube iteration B 1818 is set to height 1808 of image cropping rectangular cube iteration A 1817 plus a large error margin (S1711). The resulting 3-dimensional Cropped Image Dataset Iteration B is given by 1805 (S1706-S1707). Automatic registration is then performed on this dataset by searching for fiducial marker objects 1004 (S1708).

Regarding iteration C, length 1813 and depth 1815 of the image cropping rectangular cube iteration C 1819 are equal to the length 1807 and depth 1809 of the image cropping rectangular cube iteration A 1817 plus a large error margin. The height 1814 of the image cropping rectangular cube iteration C 1819 is set to height 1811 of image cropping rectangular cube iteration B 1818. The resulting 3-dimensional cropped image dataset iteration C is given by 1806.

Automatic registration is then performed on this dataset by searching for fiducial marker objects 1004.

If a fourth cropping (Iteration D) is needed, then the length, depth, and height of the image cropping rectangular cube iteration D will be set based on the registration results that iteration B and iteration C yielded. For example, if iteration B found six of eight fiducials and iteration C again found only six of eight fiducials, then the height of the image cropping rectangular cube iteration D will be expanded further in an attempt to find the remaining two fiducials. Automatic registration is then performed on this dataset by searching for fiducial marker objects 1004.

Figure 19:
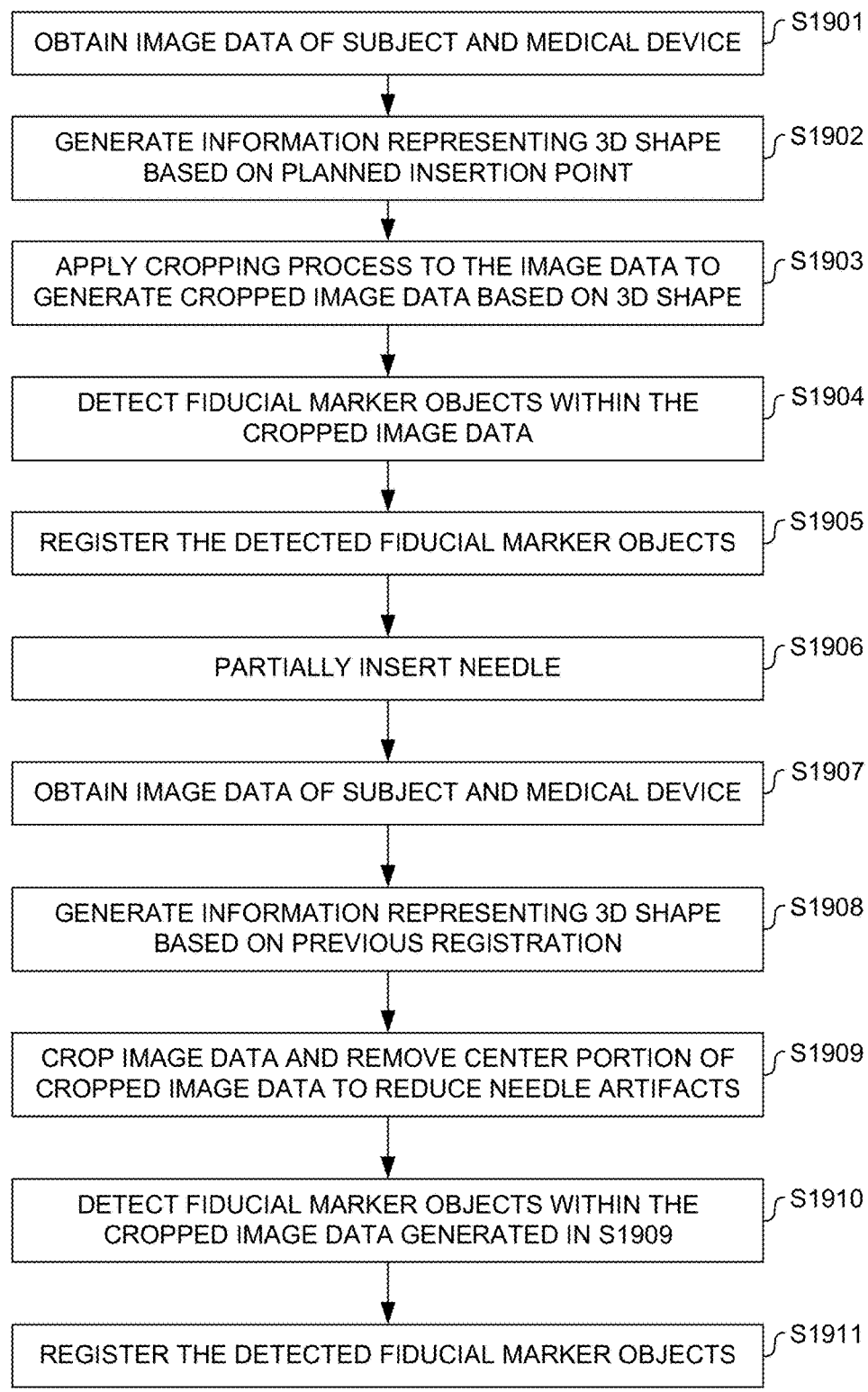
FIG. 19 is a flow diagram illustrating a process of cropping image data in accordance with some embodiments.

FIG. 19 illustrates an example flow of operations at the computing system 200 running the navigation software 100. In some embodiments, operations described with respect to FIG. 19 are carried out when a calibration image is obtained from the MRI System 104. The operations of FIG. 19 are described with reference to FIG. 20.

Steps S1901 to S1905 correspond to steps S1101-S1105. In Step S1906 a needle is partially inserted into needle insertion point 802 shown on FIG. 8. Steps S1907 to S1911 are described with reference to FIGS. 20(A)-20(C).

FIG. 20(A) depicts the medical image dataset 1005 in which automated cropping will be performed. In FIG. 20(A), it is assumed that the medical device 800 has fiducial markers 801 which are arranged in a circular layout (as shown in FIG. 8) with the physical needle insertion point 802 at the center. Since interventional procedures guided with medical imaging are an iterative process, it is common to re-register the device position with every image dataset obtained (S1907). After the first registration (S1901 to S1905) of the device position in the images the image cropping rectangular cube 2001 can be shrunk for re-registrations (S1911) to include just the device position plus some error margin to account for patient movement and breathing to further limit the fiducial search area and reduce fiducial misdetections. A 3-dimensional representation of the image cropping rectangular cube 2002 is shown in FIG. 20(B) for reiteration and clarity of cropping in 3-dimensions (not just 2-dimensions) (S1908). Since the fiducials are in a circular layout with the physical needle insertion point 802 at the center, a cylindrical cropping area 2003 can also be removed from the image cropping rectangular cube at the center (S1909). This approach causes the removal of high intensity needle artifacts 2005 in the cropped image dataset 2006 used to search for fiducial marker objects 1004 (FIG. 20(C)). This aids in the removal of needle artifacts which can be mistakenly detected as fiducial markers.

In step S1910 detection of fiducials in the cropped image data 2006 is performed. Then, in step S1911, the fiducials identified in step S1910 are registered.

Detection and Registration

Detection and registration may be performed according to any suitable method of registration. For example, detection of fiducials and registration may be performed in the manner described in U.S. Patent Publication No. 2017/0000581, which is incorporated by reference herein in its entirety. The fiducial markers objects from the medical image data are detected. To do this, first a feature enhancement, such as a derivative-based operation may be applied to the data. Next, feature extraction may be applied. Representative points are then defined. The next step involves registering the fiducial marker objects. For embodiments where the fiducials are arranged in a ring shape, the ring is rotated or flipped. This may be a full or partial rotation or a 180° flip. Then, a point-to-point matching is applied. From the data in the point-to-point matching, a target on the image is defined.

The target coordinates are computed with respect to the device based on the registration. Then, the device is adjusted to guide the needle to the target.

The above description serves to explain principles of the present disclosure; but the present disclosure should not be limited to the examples described above. For example, the order and/or timing of some of the various operations may vary from the examples given above without departing from the scope of the present disclosure. Further by way of example, the type of network and/or computing systems may vary from the examples given above without departing from the scope of the present disclosure. Other variations from the examples given above may also exist without departing from the scope of the present disclosure. While particular examples of GUIs are illustrated, it will be understood that various other implementations of GUIs are within the scope of the present disclosure. For example, various features of the illustrated examples could be modified, rearranged, or removed, or one or more features could be added without departing from the scope of the present disclosure.

The scope of the present disclosure includes a computer-readable medium storing instructions that, when executed by one or more processors, cause the one or more processors to perform one or more embodiments described herein. Examples of a computer-readable medium include a hard disk, a floppy disk, a magneto-optical disk (MO), a compact-disk read-only memory (CD-ROM), a compact disk recordable (CD-R), a CD-Rewritable (CD-RW), a digital versatile disk ROM (DVD-ROM), a DVD-RAM, a DVD-RW, a DVD+RW, magnetic tape, a nonvolatile memory card, and a ROM. Computer-executable instructions can also be supplied to the computer-readable storage medium by being downloaded via a network.

While the present disclosure has been described with reference to exemplary embodiments, it is to be understood that the present disclosure is not limited to the exemplary embodiments described.

What is claimed is:

1. A method comprising:
a light focusing element configured to focus a light along the optical axis of the apparatus,
obtaining image data of a subject and a medical device, the medical device including fiducial markers, wherein the image data includes three-dimensional image data;
generating information representing a three-dimensional shape based on a planned insertion point for performing a medical procedure;
applying a cropping process to the image data to generate cropped image data corresponding to a portion of the image data based on the three-dimensional shape, the cropped image data including image data of at least two of the fiducial markers;
detecting fiducial marker objects within the cropped image data; and
registering the fiducial marker objects by matching a model of the fiducial markers with the fiducial marker objects,
wherein, in a case where the portion of the image data includes artifact image data, the artifact image data is removed in the cropped image data.

2. The method of claim 1, wherein the fiducial markers are arranged as a fiducial frame on the medical device, the fiducial frame comprising the fiducial markers in a substantially planar arrangement.

3. The method of claim 1, wherein the fiducial markers are arranged as a fiducial frame on the medical device, the fiducial frame comprising the fiducial markers in a ring-shaped arrangement, wherein the arrangement of the fiducial markers is asymmetrical.

4. The method of claim 1, wherein the medical device includes at least three fiducial markers.

5. The method of claim 1, wherein the three-dimensional shape is spherical.

6. The method of claim 1, wherein the three-dimensional shape is cuboidal.

7. The method of claim 1, wherein a size of the three-dimensional shape is based on a size of the medical device.

8. The method of claim 1, further comprising:
obtaining information indicating the planned insertion point for performing the medical procedure.

9. The method of claim 8, wherein the information indicating the planned insertion point for performing the medical procedure is based on one or more inputs received via a user interface presenting the image data on a display of a medical imaging computing system.

10. The method of claim 1, further comprising:
determining a planned needle trajectory for performing a medical procedure,
wherein an orientation of the three-dimensional shape is along the planned needle trajectory.

11. The method of claim 1, wherein the cropping process is an iterative process that includes:
generating intermediate cropped image data by performing cropping; and
cropping the intermediate cropped image data to generate the cropped image data.

12. The method of claim 1, further comprising:
identifying a skin plane,
wherein an orientation of the three-dimensional shape is based on the skin plane.

13. The method of claim 1, wherein the artifact image data is centrally located within the portion of the image data.

14. The method of claim 1, wherein the image data includes at least one of magnetic resonance image data and computed tomography image data.

15. The method of claim 1, wherein detecting the fiducial marker objects within the cropped image data comprises identifying, within the cropped image data, all of the fiducial markers included on the medical device.

16. The method of claim 1, wherein the image data of the subject includes anatomical image data corresponding to an anatomical structure, wherein the cropped image data does not include the anatomical image data corresponding to the anatomical structure.

17. The method of claim 1, wherein the image data of the subject includes structure image data corresponding to an artificial structure, wherein the cropped image data does not include the structure image data corresponding to the artificial structure.

18. The method of claim 1, wherein the cropping process is executed automatically based on the planned insertion point for performing the medical procedure, and without requiring an additional user input operation, and
wherein detecting the fiducial marker objects within the cropped image data comprises performing a detecting process that is limited to the cropped image data.

19. A system comprising:
a medical device including fiducial markers; and
a computing system including a computer-readable storage medium storing executable program instructions, which when executed by the computing system, cause the computing system to:
obtain image data of a subject and the medical device, wherein the image data includes three-dimensional image data;
generate information representing a three-dimensional shape based on a planned insertion point for performing a medical procedure;
apply a cropping process to the image data to generate cropped image data corresponding to a portion of the image data based on the three-dimensional shape, the cropped image data including image data of at least two of the fiducial markers;
detect fiducial marker objects within the cropped image data; and
register the fiducial marker objects by matching a model of the fiducial markers with the fiducial marker objects,
wherein, in a case where the portion of the image data includes artifact image data, the artifact image data is removed in the cropped image data.

20. A computer-readable storage medium storing executable program instructions, which when executed by a computing system with one or more processors, cause the computing system to:
obtain image data of a subject and a medical device, the medical device including fiducial markers, wherein the image data includes three-dimensional image data;
generate information representing a three-dimensional shape based on a planned insertion point for performing a medical procedure;
apply a cropping process to the image data to generate cropped image data corresponding to a portion of the image data based on the three-dimensional shape, the cropped image data including image data of at least two of the fiducial markers;
detect fiducial marker objects within the cropped image data; and
register the fiducial marker objects by matching a model of the fiducial markers with the fiducial marker objects,
wherein, in a case where the portion of the image data includes artifact image data, the artifact image data is removed in the cropped image data.

* * * * *

UNITED STATES PATENT AND TRADEMARK OFFICE
CERTIFICATE OF CORRECTION

Page 1 of 1

PATENT NO. : 10,893,911 B2
APPLICATION NO. : 16/194012
DATED : January 19, 2021
INVENTOR(S) : Barret Daniels and Takahisa Kato It is certified that error appears in the above-identified patent and that said Letters Patent is hereby corrected as shown below:

In the Claims

Column 22, Lines 41-42, Claim 1: delete "a light focusing element configured to focus a light along the optical axis of the apparatus,"

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*